United States Patent
Jain et al.

(10) Patent No.: US 9,452,224 B2
(45) Date of Patent: *Sep. 27, 2016

(54) SIALIC ACID DERIVATIVES FOR PROTEIN DERIVATISATION AND CONJUGATION

(71) Applicant: Lipoxen Technologies Limited, London (GB)

(72) Inventors: Sanjay Jain, London (GB); Peter Laing, London (GB); Gregory Gregoriadis, London (GB); Dale Howard Hreczuk-Hirst, London (GB); Ioannis Papaioannou, London (GB)

(73) Assignee: LIPOXEN TECHNOLOGIES LIMITED, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/155,855

(22) Filed: Jan. 15, 2014

(65) Prior Publication Data

US 2014/0220046 A1  Aug. 7, 2014

Related U.S. Application Data

(63) Continuation of application No. 12/897,523, filed on Oct. 4, 2010, now Pat. No. 8,653,255, which is a continuation of application No. 10/568,043, filed as application No. PCT/GB2004/003511 on Aug. 12, 2004, now Pat. No. 7,807,824.

(30) Foreign Application Priority Data

Aug. 12, 2003 (EP) .................................... 03254989

(51) Int. Cl.
*C08B 37/00* (2006.01)
*C07H 15/04* (2006.01)
*A61K 47/48* (2006.01)
*C07H 3/06* (2006.01)
*C07K 17/12* (2006.01)
*A61K 31/702* (2006.01)
*A61K 31/726* (2006.01)
*C07H 5/06* (2006.01)

(52) U.S. Cl.
CPC ....... *A61K 47/48246* (2013.01); *A61K 31/702* (2013.01); *A61K 31/726* (2013.01); *A61K 47/484* (2013.01); *A61K 47/4823* (2013.01); *C07H 3/06* (2013.01); *C07H 5/06* (2013.01); *C07H 15/04* (2013.01); *C07K 17/12* (2013.01); *C08B 37/00* (2013.01); *C08B 37/006* (2013.01); *C08B 37/0006* (2013.01); *C08B 37/0063* (2013.01)

(58) Field of Classification Search
None
See application file for complete search history.

(56) References Cited

U.S. PATENT DOCUMENTS

| | | | |
|---|---|---|---|
| 4,356,170 A | 10/1982 | Jennings et al. | |
| 5,097,020 A | 3/1992 | Anderson et al. | |
| 5,329,028 A | 7/1994 | Ashkenazi et al. | |
| 5,352,670 A * | 10/1994 | Venot et al. | 514/54 |
| 5,576,002 A | 11/1996 | Jennings et al. | |
| 5,846,951 A | 12/1998 | Gregoriadis et al. | |
| 7,691,826 B2 * | 4/2010 | Hreczuk-Hirst et al. | 514/49 |
| 7,807,824 B2 | 10/2010 | Jain et al. | |
| 8,299,015 B2 | 10/2012 | Jain et al. | |
| 8,299,026 B2 | 10/2012 | Jain et al. | |
| 8,653,255 B2 * | 2/2014 | Jain et al. | 536/55.1 |
| 2006/0270830 A1 | 11/2006 | Hreczuk-Hirst et al. | |
| 2010/0022441 A1 | 1/2010 | Jain et al. | |
| 2013/0144043 A1 | 6/2013 | Jain et al. | |

FOREIGN PATENT DOCUMENTS

| | | |
|---|---|---|
| EP | 0454898 A1 | 11/1991 |
| JP | H3-284698 A | 12/1991 |
| JP | H6508610 A | 9/1994 |
| RU | 2105568 C1 | 2/1998 |
| WO | WO9222331 A1 | 12/1992 |
| WO | WO0187922 A2 | 11/2001 |

OTHER PUBLICATIONS

Roy et al., "Synthesis of protein conjugates and analogues of N-acetylneuraminic acid" Canadian Journal of Chemistry (1990) vol. 68 pp. 2045-2054.*
Bendele, "Short Communication: Renal Tubular Vacuolation in Animals Treated with Polyethylene-Glycol-Conjugated Proteins," Toxicological Sciences, Apr. 1998, vol. 42, No. 2, pp. 152-157.
Beranova, et al., "Effect of Cytochrome P-450 Inhibition and Stimulation on Intensity of Polyethylene Degradation in Microsomal Fraction of Mouse and Rat Livers," Biomaterials 1990, vol. 11 521-524.
Brocchini, "Polymers in Medicine: A Game of Chess," Drug Discovery Today, 8, (2003) pp. 111-112.
Cheng, et al., "Accelerated Clearance of Polyethylene Glycol Modified Proteins by Anti-Polyethylene Glycol IgM," Bioconjugate Chemistry, 10 (1999) pp. 520-528.
Cho, et al. "Polysialic Acid Engineering: Synthesis of Polysialylated Neoglycosphingolipid by Using the Polytransferase from Neuroinvasive *Escherichia coli* K1," Proceedings of the National Academic Sciences, USA, 91 (1994) pp. 11427-11431.

(Continued)

*Primary Examiner* — Eric Olson
(74) *Attorney, Agent, or Firm* — One3 IP Management, P.C.; Annette S. Parent; Dean G. Stathakis

(57) ABSTRACT

Derivatives are synthesized of starting materials, usually polysaccharides, having sialic acid at the reducing terminal end, in which the reducing terminal unit is transformed into an aldehyde group. Where the polysaccharide has a sialic acid unit at the non-reducing end it may be passivated, for instance by converting into hydroxyl-substituted moiety. The derivatives may be reacted with substrates, for instance containing amine or hydrazine groups, to form non-cross-linked polysialylated compounds. The substrates may, for instance, be therapeutically useful drugs peptides or proteins or drug delivery systems.

17 Claims, 23 Drawing Sheets

(56) References Cited

OTHER PUBLICATIONS

Conover, et al., "Physiological Effect of Polyethylene Glycol Conjugation on Stroma-Free Bovine Hemogiobin in the Conscious Dog After Partial Exchange Transfusion," Artificial Organ, 21 (1997) pp. 369-378.

Fernandes, et al., "The Effect of Polysialylation on the Immunogenicity and Antigenicity of Asparaginase: Implications in its Pharmacokinetics," International Journal of Pharmaceutics, 217.

Gregoriadis, et al., "Drug and Vaccine Delivery Systems," World Markets Research Centre Limited, London (2001) pp. 172-176.

Gregoriadis, et al., "Polysialic Acids: Potential for long circulating drug, protein, liposome, and other microparticle constructs," in Targeting of Drugs, Stealth Therapeutic Systems, Gregoriadis and McCormack (eds), Plenum Press (1998) pp. 193-205.

Gregoridas, et al.,"Polysialic acids: potential in improving the stability and pharmacokinetics of proteins and other therapeutics," Cellular and Molecular Life Sciences (2000) vol. 57, pp. 1964-1969.

Gregoriadis, et al., "Polysialic acids: potential in drug delivery," FEBS Letters (1993) 315, pp. 271-276.

Hreczuk-Hirst, et al., Preparation and properties of polysialylated interferon-a-2b, AAPS Annual Meeting, (2002) Toronto, Canada, M1056.

International Preliminary Report on Patentability for PCT/GB2004003511, completed Jul. 4, 2005, 7 pages.

International Search Report for PCT/GB2004/003511, mailed on Nov. 12, 2004, 5 pages.

Hunter, et al., "Therapeutic synthetic polymers: a game of Russian roulette," Drug Discovery Today (2002) 7:998-1001.

Jain, et al., "Polysialylated insulin: synthesis, characterization and biological activity in vivo," Biochim. Biophys. Acta (2003) 1622, pp. 42-49.

Jain, et al., "Polysialylation: the natural way to improve the stability and pharmacokinetics of protein and peptide drugs," Drug Delivery Systems and Sciences (2004) 4(2): 3-9.

Jennings, et al., "Immunochemistry of groups A, B, and C meningococcal polysaccharide-tetanus toxoid conjugates," Journal of Immunology (1981) 127: 1011-1018.

Lifely, et al.,"Sialic acid polysaccharide antigens of Neisseria meningitidis and *Escherichia coli*: esterification between adjacent residues," Carbohydrate Research (1981) 94, pp. 193-203.

Muhlenhoff, et al., "Polysialic acid: three-dimensional structure, biosynthesis and fucnction," Current Opinions in Sructural Biology, No. 8 (1998), pp. 558-564.

Park, et al., "A Submicrodetermination of Glucose," Journal of Biological Chemistry, (1949), vol. 181, pp. 149-151.

Rutishauser, "Polysialic Acid as a Regulator of Cell Interactions" Neurobiology of Glycoconjugates, pp. 367-382, Plenum Press, New York, 1989.

Sen, et al., The specificity of the bindng site of Achatinin H, a sialic acid-binding lectin from Achatina fulica, Carbohydrate Research, (1995) pp. 115-125.

Svennerholm, "Quantitative Estimation of Sialic Acid II: A Colorimetric Resorcinol-Hydrochloric Acid Method," Biochemca Et Biophysica Acta, vol. 24 (1957), pp. 604-611.

Written Opinion of the International Searching Authority for PCT/GB2004/003511, dated Nov. 11, 2004, 9 pages.

\* cited by examiner

Monofunctional polysialic acid cannot form unintended by-products described for periodate-oxidised natural polysialic acid in Fig. 3

Figure 10: A typical native page of colominic acid fractions with m.w. (B = broad dispersed; N= narrow dispersed)

1  11 KDa, B
2  22 KDa, B
3  8.06 KDa, N
4  12.49 KDa, N
5  14.47 KDa, N
6  16.02 KDa, N
7  20.46 KDa, N
8  23.46 KDa, N
9  31.20 KDa, N
10 34.49 KDa, N
11 39.08 KDa, N
12 11 KDa, B
13 22 KDa, B
14 39 kDa, B

Figure 12: A typical GPC chromatogram for CA fractions

Figure 13: Colominic acid samples from different steps of fractionation 1) 18.7 kDa disperse
2) 32.2 kDa from IEC
3) 32.2 kDa ultrafiltered
4) 32.2 kDa post oxidation
5) 40.9 kDa from IEC
6) 40.9 Kda ultrafiltered
7) 49.0 KDa post oxidation Figure 14: Fractionation by ultrafiltration 1 Markers
2 GH
3 GH + 22.7 kDaCA (pd=1.34)
4 GH +27.7 K Da ( pd=.109)
5 GH + 40.9 kDa CA ( pd=1.02)
6 GH+CA 1 Fraction 3
2 Fraction 2
3 Fraction 1
4 Unbound
5 GH
6 Markers

Figure 18

Table 6: Ion exchange chromatography of CA22.7: Scale up (75ml matrix, 3g of CA)

| Elution buffers (in 20mM Triethanolmine buffer+mM NaCl, pH7.4) | M.W. | Pd | % Population |
|---|---|---|---|
| 325 mM | 12586 | 1.091 | 77.4% |
| 350 mM | 20884 | 1.037 | 3.2% |
| 375 mM | 25542 | 1.014 | 5.0% |
| 400 mM | 28408 | 1.024 | 4.4% |
| 425 mM* | | | 7.4% |
| 450 mM | 43760 | 1.032 | 2.3% |
| 475 mM | 42921 | 1.096 | 0.2% |

*Not done

SIALIC ACID DERIVATIVES FOR PROTEIN DERIVATISATION AND CONJUGATION

CROSS-REFERENCE TO RELATED APPLICATIONS

This application is a continuation of U.S. application Ser. No. 12/897,523, filed on Oct. 4, 2010, which is a continuation of U.S. application Ser. No. 10/568,043, having a 371(c) filing date of Dec. 1, 2006, now U.S. Pat. No. 7,807,824, which is the national phase of PCT application PCT/GB2004/003511 having an international filing date of Aug. 12, 2004, which claims priority from European application 03254959.1 filed Aug. 12, 2003. The contents of these documents are incorporated herein by reference.

FIELD OF THE INVENTION

The present invention relates to derivatives of compounds such as polysaccharides having at least terminal sialic units, and preferably consisting essentially only of sialic acid units, having an aldehyde group for reaction with substrates at the reducing terminal end and methods of producing them. The derivatives are useful for conversion to other reactive derivatives and for conjugation to amine-group containing substrates such as peptides, proteins, drugs, drug delivery systems (e.g. liposomes), viruses, cells, e.g. animal cells, microbes, synthetic polymers etc.

Polysialic acids (PSAs) are naturally occurring unbranched polymers of sialic acid produced by certain bacterial strains and in mammals in certain cells [Roth et. al., 1993]. They can be produced in various degrees of polymerisation from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist—such as the alternating alpha-2,8 alpha-2,9 polysialic acid of *E. coli* strain K92 and group C polysaccharides of *N. meningitidis*. Sialic acid may also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) [Muhlenhoff et. al., 1998; Rutishauser, 1989; Troy, 1990, 1992; Cho and Troy, 1994], although there are no known receptors for polysialic acids in mammals. The alpha-2,8-linked polysialic acid of *E. coli* strain K1 is also known as 'colominic acid' and is used (in various lengths) to exemplify the present invention.

The alpha-2,8 linked form of polysialic acid, among bacterial polysaccharides, is uniquely non-immunogenic (eliciting neither T-cell or antibody responses in mammalian subjects, even when conjugated to immunogenic carrier proteins) which may reflect its status as a mammalian (as well as a bacterial) polymer. Shorter forms of the polymer (up to n=4) are found on cell-surface gangliosides, which are widely distributed in the body, and are believed to effectively impose and maintain immunological tolerance to polysialic acid. In recent years, the biological properties of polysialic acids, particularly those of the alpha-2,8 linked homopolymeric polysialic acid, have been exploited to modify the pharmacokinetic properties of protein and low molecular weight drug molecules [Gregoriadis, 2001; Jain et. al., 2003; U.S. Pat. No. 5,846,951; WO-A-0187922]. Polysialic acid derivatisation gives rise to dramatic improvements in circulating half-life for a number of therapeutic proteins including catalase and asparaginase [Fernandes and Gregoriadis, 1996 and 1997], and also allows such proteins to be used in the face of pre-existing antibodies raised as an undesirable (and sometimes inevitable) consequence of prior exposure to the therapeutic protein [Fernandes and Gregoriadis, 2001]. In many respects, the modified properties of polysialylated proteins are comparable to proteins derivatised with polyethylene glycol (PEG). For example, in each case, half-lives are increased, and proteins and peptides are more stable to proteolytic digestion, but retention of biological activity appears to be greater with PSA than with PEG [Hreczuk-Hirst et. al., 2002]. Also, there are questions about the use of PEG with therapeutic agents that have to be administered chronically, since PEG is only very slowly biodegradable [Beranova et al., 2000] and high molecular weight forms tend to accumulate in the tissues [Bendele, et al., 1998; Conyers, et al., 1997]. PEGylated proteins have been found to generate anti PEG antibodies that could also influence the residence time of the conjugate in the blood circulation [Cheng et. al., 1990]. Despite, the established history of PEG as a parenterally administered polymer conjugated to therapeutics, a better understanding of its immunotoxicology, pharmacology and metabolism will be required [Hunter and Moghimi, 2002; Brocchini, 2003]. Likewise there are concerns about the utility of PEG in therapeutic agents that may require high dosages, since accumulation of PEG may lead to toxicity. The alpha-2,8 linked polysialic acid (PSA) therefore offers an attractive alternative to PEG, being an immunologically invisible biodegradable polymer which is naturally part of the human body, and which degrades, via tissue neuraminidases, to sialic acid, a non-toxic saccharide.

Our group has described, in previous scientific papers and in granted patents, the utility of natural polysialic acids in improving the pharmacokinetic properties of protein therapeutics [Gregoriadis, 2001; Fernandes and Gregoriadis; 1996, 1997, 2001; Gregoriadis et. al., 1993, 1998, 2000; Hreczuk-Hirst et. al., 2002; Mital, 2004; Jain et. al., 2003, 2004; U.S. Pat. No. 5,846,951; WO-A-0187922]. Now, we describe new derivatives of PSAs, which allow new compositions and methods of production of PSA-derivatised proteins (and other forms of therapeutic agent). These new materials and methods are particularly suitable for the production of PSA-derivatised therapeutic agents intended for use in humans and animals, where the chemical and molecular definition of drug entities is of major importance because of the safety requirements of medical ethics and of the regulatory authorities (e.g. FDA, EMEA).

Methods have been described previously for the attachment of polysaccharides to therapeutic agents such as proteins [Jennings and Lugowski, 1981; U.S. Pat. No. 5,846, 951; WO-A-0187922]. Some of these methods depend upon chemical derivatisation of the 'non-reducing' end of the polymer to create a protein-reactive aldehyde moiety (FIG. 1). This is because the reducing end of PSA and other polysaccharides is only weakly reactive with proteins under the mild conditions necessary to preserve protein conformation and the chemical integrity of PSA and protein during conjugation. A non-reducing sialic acid terminal unit, since it contains vicinal diols, can be readily (and selectively)

oxidised with periodate to yield a mono-aldehyde form, which is much more reactive towards proteins, and which comprises a suitably reactive element for the attachment of proteins via reductive amination and other chemistries. We have described this previously in U.S. Pat. No. 5,846,951 and WO-A-0187922. The reaction is illustrated in FIG. 1 in which a) shows the oxidation of colominic acid (alpha-2,8 linked polysialic acid from E. coli) with sodium periodate to form a protein-reactive aldehyde at the non-reducing end and b) shows the selective reduction of the Schiff's base with sodium cyanoborohydride to form a stable irreversible covalent bond with the protein amino group.

Of the various methods, which have been described to attach polysialic acids to therapeutic agents [U.S. Pat. No. 5,846,951; WO-A-0187922], none of these are specifically intended to conjugate via the reducing end, because of its weak reactivity towards therapeutic proteins. Although theoretically a useful reaction, achievement of acceptable yields of conjugate via reaction of proteins with the hemiketal of the reducing end of the PSA requires reaction times that are not conducive to protein stability. Secondly, reactant concentrations (of polymer excess) are required that may be unattainable or uneconomical. Nevertheless, despite the inefficiency of this reaction, we have observed that it gives rise to unintentional by-products during conjugation reactions intended to produce conjugates with protein via an introduced aldehyde at the (opposite) non-reducing end of the polymer. The potential for such by-products is evident in published studies of catalase, insulin and asparaginase [Fernandes and Gregoriadis, 1996, 1997, 2001; Jain et. al., 2003], where the hemiketal of the natural (chemically unmodified) form of the polymer gives rise to protein conjugates at a low level of efficiency (less than 5% of protein becoming derivatised, see further below in the reference examples, and table 1) during reductive amination.

The reactivity of the reducing end of colominic acid, though weak towards protein targets, is sufficient to be troublesome in the manufacture of chemically defined conjugates of the kind likely to be preferred by regulatory authorities for therapeutic use in man and animals. Unlike the natural colominic acid polymer, which is weakly monofunctional, the periodate oxidised form of PSA (having an aldehyde at one end and a hemiketal at the other) inevitably gives rise to a complexity of products which seriously complicate the task of producing a molecularly defined and pharmaceutically acceptable conjugate (FIG. 2). FIG. 2a is a schematic diagram showing the formation of by-products during polysialylation (original method). FIG. 2b is a more detailed schematic diagram showing the formation of by-products during polysialylation (original method), specifically i) asymmetric dimer;
ii) linear polymer;
iii) branched polymer; and
iv) various more-complex structures.

At first sight it would seem a simple matter to purify the intended reaction product away from the various unintended products described in FIG. 2, however, this is by no means straightforward, since the physicochemical characteristics of some of the intended forms (size charge etc.) are remarkably similar, indeed almost identical, to those of the intended form of the product. This would frustrate attempts to purify out the intended species from the reaction mixture by techniques such as ion-exchange chromatography and gel-permeation chromatography (which separate on the basis of charge and size respectively), and would also frustrate many other methods of purification. Now therefore we have solved the problems by developing a new method for conjugation of polysaccharides having sialic acid groups at the reducing terminal to proteins, whereby the weak reactivity of the reducing end can be exploited to beneficial effect, and which avoids the product complexity described in FIG. 2(b) using the established method (FIG. 1) of reductive amination of proteins with periodate oxidised natural colominic acid.

Jennings and Lugowski, in U.S. Pat. No. 4,356,170, describe derivatisation of bacterial polysaccharides to proteins via an activated reducing terminal unit involving a preliminary reduction step then an oxidation step. They suggest this approach where the reducing terminal unit is N-acetyl mannosamine, glucose, glucosamine, rhamnose and ribose.

In EP-A-0454898 an amino group of a protein is bound to an aldehyde group produced by reducing and partially oxidising the reducing terminal sugar moiety of a glycosaminoglycan. The glycosaminoglycans treated in this way include hyaluronic acid, chondroitin sulphate, heparin, heparan sulphate, and dermatan sulphate. None of these compounds has a sialic acid unit at the reducing terminal.

In the invention there is provided a new process for producing an aldehyde derivative of a sialic acid compound in which a starting material having a sialic acid unit at its reducing terminal is subjected to sequential steps of a) reduction to reductively open the ring of the reducing terminal sialic acid unit whereby a vicinal diol group is formed; and b) selective oxidation to oxidise the vicinal diol group formed in step a) to form an aldehyde group.

The starting material is preferably a di-, oligo- or polysaccharide although the invention may have utility for other starting materials.

The starting material used in the process of the invention should preferably have the sialic acid unit at the reducing terminal end joined to the adjacent unit through its eight carbon atom. In step b) the 6,7-diol group is oxidised to form an aldehyde at the carbon 7 atom.

In an alternative embodiment, where the sialic acid unit at the reducing terminal end is joined to the adjacent unit through the 9 carbon atom, in step b) a 7,8 diol group is formed and is oxidised to form an aldehyde on the 8 carbon atom.

In the process of the invention, where the starting material is a di-, oligo- or poly-saccharide, it is preferred that the starting material has a terminal saccharide unit at the non-reducing end which has a vicinal diol group and in which the starting material is subjected to a preliminary step, prior to step a), of selective oxidation to oxidise the vicinal diol group to an aldehyde, whereby in step a) the aldehyde is also reduced to form a hydroxy group which is not part of a vicinal diol group. The invention is of particular utility where the terminal unit of the reducing end of the starting material is a sialic acid unit. In an alternative embodiment the starting material may have a vicininal diol group which is retained as such at a non-reducing terminal saccharide unit of the starting material for step a). It will not be modified by the reduction step, but will be oxidised in the oxidation step to form an aldehyde group. The product will be di-functional and may have useful therapeutic activities derived from its ability to cross-link substrates by reaction at both aldehyde groups with suitable functional groups on the substrate.

According to a second aspect of the invention there is provided a new process in which a sialic acid starting material having a terminal sialic acid at a non-reducing terminal end is subjected to the following steps:

c) a selective oxidation step to oxidise the non-reducing terminal sialic acid unit at the 7,8 vicinal diol group to form a 7-aldehyde; and d) a reduction step to reduce the 7-aldehyde group to the corresponding alcohol. This aspect of the invention provides sialic acid derivatives which have a passivated non-reducing terminal, allowing activation of the reducing terminal for subsequent reaction. The activation may be a reduction/oxidation process e.g. of the first aspect of the invention, with optional subsequent steps of converting the aldehyde group into another group, such as amination to form an amine. Other steps for activating the reducing terminal may be devised.

Preferably this second aspect of the invention is part of a process in which the starting material has a reducing terminal unit and is required to be subsequently conjugated to another molecule through that unit. In such a process the reducing terminal unit is generally activated for instance by a reaction which would otherwise have activated a proportion of the sialic acid non-reducing terminal units were it not for the passivation process. Such a reaction is, for instance selective oxidation of a vicinal diol moiety and is carried out after step d).

In the invention the preferred polysaccharide starting material may comprise units other than sialic acid in the molecule. For instance sialic acid units may alternate with other saccharide units. Preferably, however, the polysaccharide consists substantially only of units of sialic acid. Preferably these are joined 2-8 and/or 2-9.

Preferably the polysaccharide starting material has at least 2, more preferably at least 5, more preferably at least 10, for instance at least 50, saccharide units. For instance a polysaccharide may comprise at least 5 sialic acid units.

The polysialic acid may be derived from any source preferably a natural source such as a bacterial source, e.g. *E. coli* K1 or K92, group B meningococci, or even cow's milk or N-CAM the sialic acid polymer may be a heteropolymeric polymer such as group 135 or group V of *N. meningitidis*. The polysialic acid may be in the form of a salt or the free acid. It may be in a hydrolysed form, such that the molecular weight has been reduced following recovery from a bacterial source. The polysialic acid may be material having a wide spread of molecular weights such as having a polydispersity of more than 1.3, for instance as much as 2 or more. Preferably the polydispersity of molecular weight is less than 1.2, for instance as low as 1.01.

A population of polysialic acids having a wide molecular weight distribution may be fractionated into fractions with lower polydispersities, i.e. into fractions with differing average molecular weights. Fractionation is preferably anion exchange chromatography, using for elution a suitable basic buffer. We have found a suitable anion exchange medium i) a preparative medium such as a strong ion-exchange material based on activated agarose, having quaternary ammonium ion pendant groups (ie strong base). The elution buffer is non-reactive and is preferably volatile so that the desired product may be recovered from the base in each fraction by evaporation. Suitable examples are amines, such as triethanolamine. Recovery may be by freeze-drying for instance. The fractionation method is suitable for a polysialic acid starting material as well as to the derivatives. The technique may thus be applied before or after the essential process steps of this invention.

It is believed this is the first time ion-exchange chromatography has been applied to fractionate an ionic polysaccharides with molecular weights above about 5 kDa especially polysialic acid of such MWs on the basis of molecular weight. According to a further aspect of this invention there is provided a process for fractionating a population of ionisable polysaccharide with MW higher than 5 kDa using ion-exchange chromatography using in the elution buffer a base or acid which is preferably volatile. Preferably the polysaccharide has carboxylic acid groups and the ion-exchange is anion exchange. Preferably the elution buffer contains an amine, more preferably triethanolamine. Most preferably the polysaccharides are recovered from the fractions by freeze-drying. This method can be applied for the fractionation of CA having other reactive moieties (maleimide or iodoacetate etc.) and other natural (e.g. dextran sulphate) and synthetic (e.g. polyglutamic acid; polylysine in the later case by cation exchange chromatography) charged polymers. It is believed that it is also the first time that IEC has been used to separate ionic polysaccharides in combination with precipitation techniques and/or ultrafiltration methods. The IEC method should remove by-products of production which remain in the commercially available PSAs and CAs, such as endotoxins.

In a preliminary oxidation step and step c) the selective oxidation should preferably be carried out under conditions such that there is substantially no mid-chain cleavage of the backbone of a long-chain (polymeric) starting material, that is, substantially no molecular weight reduction. Enzymes which are capable of carrying out this step may be used. Most conveniently the oxidation is a chemical oxidation. The reaction may be carried out with immobilised reagents such as polymer-based perrhuthenate. The most straight forward method is carried out with dissolved reagents. The oxidant is suitably perrhuthenate, or, preferably, periodate. Oxidation may be carried out with periodate at a concentration in the range 1 mM to 1M, at a pH in the range 3 to 10, a temperature in the range 0 to 60° C. for a time in the range 1 min to 48 hours.

In the process, step a) is a step in which the sialic acid unit at the reducing end is reduced. Usually the unit at the reducing end of the starting material is in the form of a ketal ring and reduction in step a) opens the ring and reduces the ketone to an alcohol. The hydroxyl group at the 6-carbon atom is thus part of a vicinal diol moiety.

Suitable reduction conditions (for steps a) and d)) may utilise hydrogen with catalysts or, preferably hydrides, such as borohydrides. These may be immobilised such as Amberlite (trade mark)-supported borohydride. Preferably alkali metal hydrides such as sodium borohydride is used as the reducing agent, at a concentration in the range 1 μM to 0.1M, a pH in the range 6.5 to 10, a temperature in the range 0 to 60° C. and a period in the range 1 min to 48 hours. The reaction conditions are selected such that pendant carboxyl groups on the starting material are not reduced. Where a preliminary oxidation step has been carried out, the aldehyde group generated is reduced to an alcohol group not part of a vicinal diol group. Other suitable reducing agents are cyanoborohydride under acidic conditions, e.g. polymer supported cyanoborohydride or alkali metal cyanoborohydride, L-ascorbic acid, sodium metabisulphite, L-selectride, triacetoxyborohydride etc.

Between any preliminary oxidation step and reduction step a) and after step b) and between oxidation step c) and reduction step d) and between step d) and any subsequent oxidation step, the respective intermediate must be isolated from oxidising and reducing agents, respectively, prior to being subjected to the subsequent step. Where the steps are carried out in solution phase, isolation may be by conventional techniques such as expending excess oxidising agent using ethylene glycol, dialysis of the polysaccharide and ultrafiltration to concentrate the aqueous solution. The product mixture from the reduction step again may be separated by dialysis and ultrafiltration. It may be possible to devise reactions carried out on immobilised oxidising and reducing reagents rendering isolation of product straightforward.

The selective oxidation step, step b) is suitably carried out under similar conditions to the preliminary oxidation step as described above. Likewise the oxidation agent should be exhausted before recovery of the product using ethylene glycol. The product is subsequently recovered by suitable means such as dialysis and ultrafiltration.

The process of the first aspect of the invention and of the preferred embodiment of the second aspect which includes a subsequent oxidation step after step d) to activate a reducing terminal saccharide unit produces an activated derivative having a reactive aldehyde moiety derived from the reducing terminal. The preferred process involving an oxidation, then reduction, then oxidation step produces an activated product having a single reactive aldehyde moiety. If there is no preliminary oxidation step and the starting material has a non-reducing terminal unit which has a vicinal diol group (e.g. a sialic acid), the product will have aldehyde groups at each terminal which may have utility.

Aldehyde groups are suitable for conjugating to amine-group containing substrates or hydrazine compounds. Processes in which the activated product of an oxidation step is subsequently conjugated to substrate compound form a further aspect of the invention. Preferably the conjugation reaction is as described in our earlier publications mentioned above, that is involving conjugation with an amine to form a Schiff base, preferably followed by reduction to form a secondary amine moiety. The process is of particular value for derivatising proteins, of which the amine group is suitably the epsilon amine group of a lysine group or the N-terminal amino group. The process is of particular value for derivatising protein or peptide therapeutically active agents, such as cytokines, growth hormones, enzymes, hormones, antibodies or fragments. Alternatively the process may be used to derivatise drug delivery systems, such as liposomes, for instance by reacting the aldehyde with an amine group of a liposome forming component. Other drug delivery systems are described in our earlier case U.S. Pat. No. 5,846,951. Other materials that may be derivatised include viruses, microbes, cells, including animal cells and synthetic polymers.

Alternatively the substrate may have a hydrazine group, in which case the product is a hydrazone. This may be reduced if desired, for additional stability, to an alkyl hydrazide.

In another preferred embodiment, oxidation step b) or a subsequent oxidation step after step d) is followed by the reaction of the or each aldehyde group with a linker compound, comprising an amine group or a hydrazide group and another functional group suitable for selective derivatisation of proteins or other therapeutically active compounds or drug delivery systems. Such a linker may, for instance, comprise a compound having a functional group substituent for specific reaction with sulfhydryl groups and a di-basic organic group joining the amine or hydrazide group and the functional group. Reaction of an aldehyde moiety with the amino or hydrazide group forms a reactive conjugate suitable for binding to a substrate having a thiol (sulfhydryl) group. Such conjugates are of particular value for selective and site-directed derivatisation of proteins and peptides.

The derivatisation of proteins and drug delivery systems may result in increased half life, improved stability, reduced immunogenicity, and/or control of solubility and hence bioavailability and pharmaco-kinetic properties, or may enhance solubility actives or viscosity of solutions containing the derivatised active.

According to the invention there is also provided a novel compound which is an aldehyde derivative of a di-, oligo or polysaccharide comprising sialic acid moieties, in which the terminal unit at the reducing end is a group OR in which R is selected from

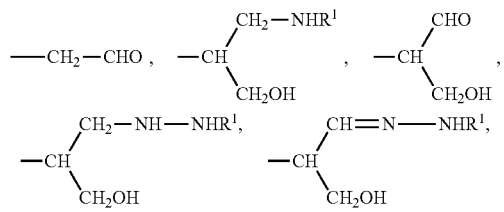

—$CH_2CH_2NHR^1$, $CH_2CH=N-NHR^1$ and $CH_2CH_2NHNHR^1$ in which $R^1$ is H, $C_{1-24}$ alkyl, aryl $C_{2-6}$ alkanoyl, or a polypeptide or a protein linked through the N terminal or the side chain amine group of a lysine residue, a drug delivery system or is an organic group having a functional substituent adapted for reaction with a sulfhydryl group and, preferably the terminal moiety at the non-reducing end is passivated.

The novel compound may comprise mid-chain saccharide units between the two terminal units. The mid-chain units may consist only of sialic acid units or, alternatively, may comprise other saccharide units in addition to the terminal units which are derived from sialic acid units. The compound may generally be formed as described above in relation to the first aspect of the invention.

The novel compound may be a polysialylated substrate, comprising at least one polysialic acid (polysaccharide) group conjugated on each molecule of substrate, the conjugation including a secondary amine, hydrazone or alkyl hydrazide linkage via the reducing terminal of the polysialic acid, and is substantially free of crosslinking via the non-reducing end of the polysialic acid group to another molecule of substrate. The substrate may be, for instance, a biologically active compound, for instance a pharmaceutically active compound, especially a peptide or protein therapeutic, or a drug delivery system. Such actives are generally as described above.

The novel compound may have the general formula I

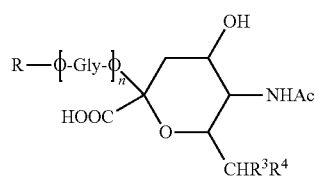

in which R is selected from

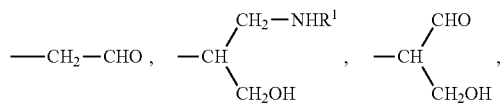

-continued

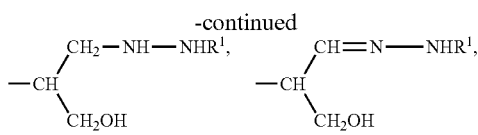

—CH$_2$CH$_2$NHR$^1$, CH$_2$CH=N—NHR$^1$ and CH$_2$CH$_2$NHNHR$^1$ in which R$^1$ is H, C$_{1-24}$ alkyl, aryl C$_{2-6}$ alkanoyl, or a polypeptide or a protein linked through the N terminal or the ε-amine group of a lysine residue, a drug delivery system or is an organic group having a functional substituent adapted for reaction with a sulfhydryl group;

R$^3$ and R$^4$ are selected from
i) R$^3$ is H and R$^4$ is OH
ii) where R is CH(CH$_2$OH)CH$_2$OH or —CH$_2$CHO, R$^3$ and R$^4$ together are =O;
iii) where R is CH(CH$_2$OH)CH$_2$NHR$^1$ or —CH$_2$CH$_2$NHR$^1$, R$^3$ is H and R$^4$ is —NHR$^1$;
iv) where R is —CH(CH$_2$OH)CH$_2$NHNHR$^1$ or —CH$_2$CH$_2$NHNHR$^1$, R$^3$ is H and R$^4$ is —NHNHR$^1$; or
v) —CH$_2$CH=N—NHR$^1$, R$^3$ and R$^4$ are together =N—NHR$^1$;

Ac is acetyl
n is 0 or more; and
GlyO is a glycosyl group.
where R is a group

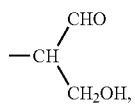

the compound of the general formula I is the polysaccharide which is polysialic acid derivative having an aldehyde group at the reducing terminal unit.
where R is a group

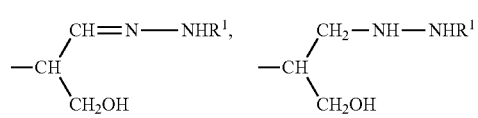

CH$_2$CH=N—NHR$^1$ or CH$_2$CH$_2$NHNHR$^1$ the compound is a conjugate formed by reacting the aldehyde derivative of the polysialic acid with a hydrazide R$^1$NHNH$_2$. A hydrazide is preferably an acyl hydrazide (R$^1$ has a terminal carbonyl group).
where R is a group

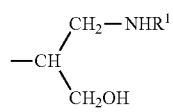

or CH$_2$CH$_2$NHR$^1$, the compound is a conjugate formed by reacting the aldehdye derivative of the polysialic acid with a primary amine group containing compound R$^1$NH$_2$.

R$^1$ may be the residue of a peptide or protein therapeutic, for instance an antibody or fragment, an enzyme or other biologically active compound as described above. The group R$^1$ may comprise a linker moiety from the active compound to the polysialic acid.

Alternatively, R$^1$ may be the residue of a linker reagent, for instance to form a derivatised polysialic acid suitable for conjugating to groups other than amine groups or hydrazides on active compounds. Examples are linker reagents of the formula

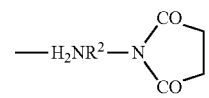

that is a N-maleimido compound, in which R$^2$ is a dibasic organic group, for instance an arylene oligo(alkoxy)alkane or, preferably, alkanediyl group, for instance a C$_{2-12}$-alkane diyl group.

The present invention is of most utility where the novel compound is mono-functional and is passivated at the terminal unit at the non-reducing end. In such compounds R$^3$ is H and R$^4$ is OH. R can be any of the meanings set out above. The glycosyl groups preferably comprise sialic acid units and more preferably consist only of such units, linked 2-8 and/or 2-9, e.g. alternating 2-8/2-9, to one another.

The invention further provides compositions comprising the novel compounds and a diluent as well as pharmaceutical compositions comprising novel compounds in which R$^1$ has biological activity, and a pharmaceutically acceptable excipient. Pharmaceutical compositions may be administered orally, intravenously, intraperitoneally, intramuscularly, subcutaneously, intranasally, intradermally, topically or intratracheally.

There is provided in a second aspect of the invention a novel compound which is the product of the process according to the second method aspect which has the general formula

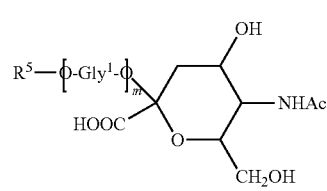

II in which Ac is acetyl;
m is 0 or more;
Gly$^1$O is glycosyl; and
R$^5$ is an organic group, preferably the reduced form of a terminal reducing saccharide unit, the oxidised derivative thereof which is an aldehyde or the reaction product of such an aldehyde, which is, for instance, an amine or a hydrazide.

Preferably R$^5$ is selected from the same groups as R above.

Alternatively R$^5$ is a group III joined via one of the carbons 8 or 9 to

(whereby the other of the carbons 8 or 9 is substituted with hydroxyl:

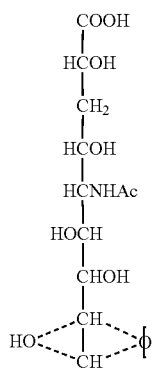

III which is the product of the ring-opening reduction of a reducing terminal sialic acid.

Preferably the groups Gly$^1$O comprise sialic acid units, most preferably consist of sialic acid units. The value of m is preferably 2 or more, more preferably 5-1000, for instance 10-500, more preferably 10 to 50.

The new method is of particular value for creation of a monofunctional polysialic acid (PSA). It is based on an understanding of the tautomeric equilibrium of the reducing end ring of PSA's for instance colominic acid (CA) which is described in FIG. 3. The reducing end sialic acid residue of PSA spontaneously forms an open ring ketone by tautomerisation (FIG. 3). In the dynamic equilibrium between ring and linear structures of the reducing end sialic acid residue, the ketone moiety is present on only a subpopulation of PSA molecules at any one instant. As mentioned above however, it is here emphasized that the reactivity of the reducing end hemiketal is insufficient to be of practical utility for the attachment of PSA to proteins, which is why previously described methods do not employ this site on the polymer for attachment to proteins or other drugs. Thus as illustrated in FIG. 3, in solution, the terminal sialic acid residue at the reducing end of polysialic acid exists in a tautomeric equilibrium. The ring-open form, although in low abundance in the equilibrium, is weakly reactive with protein amine groups, and can give rise to covalent adducts with proteins in the presence of sodium cyanoborohydride.

In the preferred embodiment of the invention, in order to achieve better defined products of protein conjugation with PSAs, we have now created a chemically modified form of polysialic acid that is monofunctional. The new form involves chemical modifications to both termini of the natural polysialic acid molecule. Unlike the original form of the reaction (FIG. 1), wherein the polymer becomes conjugated predominantly in the 2 to 8 orientation, with 'reducing end' outermost, the new form of the polymer becomes attached exclusively in the opposite orientation.

The new preferred monofunctional form of the polysialic acid or other polysaccharide aldehyde derivative is more conducive to the synthesis and manufacture of a pharmaceutically acceptable product, since it avoids the considerable complexity which is otherwise inadvertently created by use of polymer forms with unmodified reducing ends (FIG. 2). Production of the new form of the polymer (FIG. 4) involves, selective oxidation, preferably by periodate as in our previous disclosures, to introduce an aldehyde function at the non-reducing end. Unlike the prior art illustrated in FIG. 1 however, this aldehyde moiety is then destroyed by reduction, for instance with borohydride. At the other end of the polymer, the borohydride reduction step also simultaneously locks open the ring structure of the reducing end, by reducing the hemiketal. This simultaneous reduction of the ketone to a hydroxyl moiety introduces a new diol functionality which is now amenable to selective oxidation in the second oxidation step. When the natural polymer has been (successively) oxidised with periodate, reduced with borohydride, and oxidised a second time with periodate, a new polymer form is created, which is truly monofunctional, having a single reactive group (an aldehyde) only at the reducing end (FIG. 3).

The protein reactivity (by reductive amination) of the various intermediates described in the 'double oxidation' process of FIG. 4 is described in Table 2. Notably, these data demonstrate that the intermediate 'CAOR' (colominic acid—a polysialic acid—oxidised/reduced), created by borohydride reduction of the periodate oxidised polymer, is inert towards protein targets, proving that both its aldehyde and hemiketal moieties have been destroyed by borohydride reduction. In a second cycle of periodate oxidation of the 'protein inert' CAOR intermediate, a new polysialic acid derivative is created (CAORO) that is again reactive towards proteins (Table 2) and, moreover, is truly monofunctional in character, having a single aldehyde group at the 'reducing end' of the polymer, and being unreactive towards proteins at its other end. The monofunctional PSA can give rise only to single-orientation attachment to proteins, with the non-reducing end outermost, and is incapable of inadvertently cross-linking proteins (FIG. 5). This new scheme of reaction (FIG. 4), known as the 'double oxidation' method elegantly avoids the need to purify away the intended product from the various unintended products (described in FIG. 2), which are completely avoided in this new reaction scheme.

BRIEF DESCRIPTION OF THE DRAWINGS

FIG. 2b represents schematically the potential by-products of the side reactions of FIG. 2a;

FIG. 18 (Table 6) shows ion exchange chromatography of CA22.7.

DETAILED DESCRIPTION OF THE INVENTION

Examples

Materials

Figure 1A:
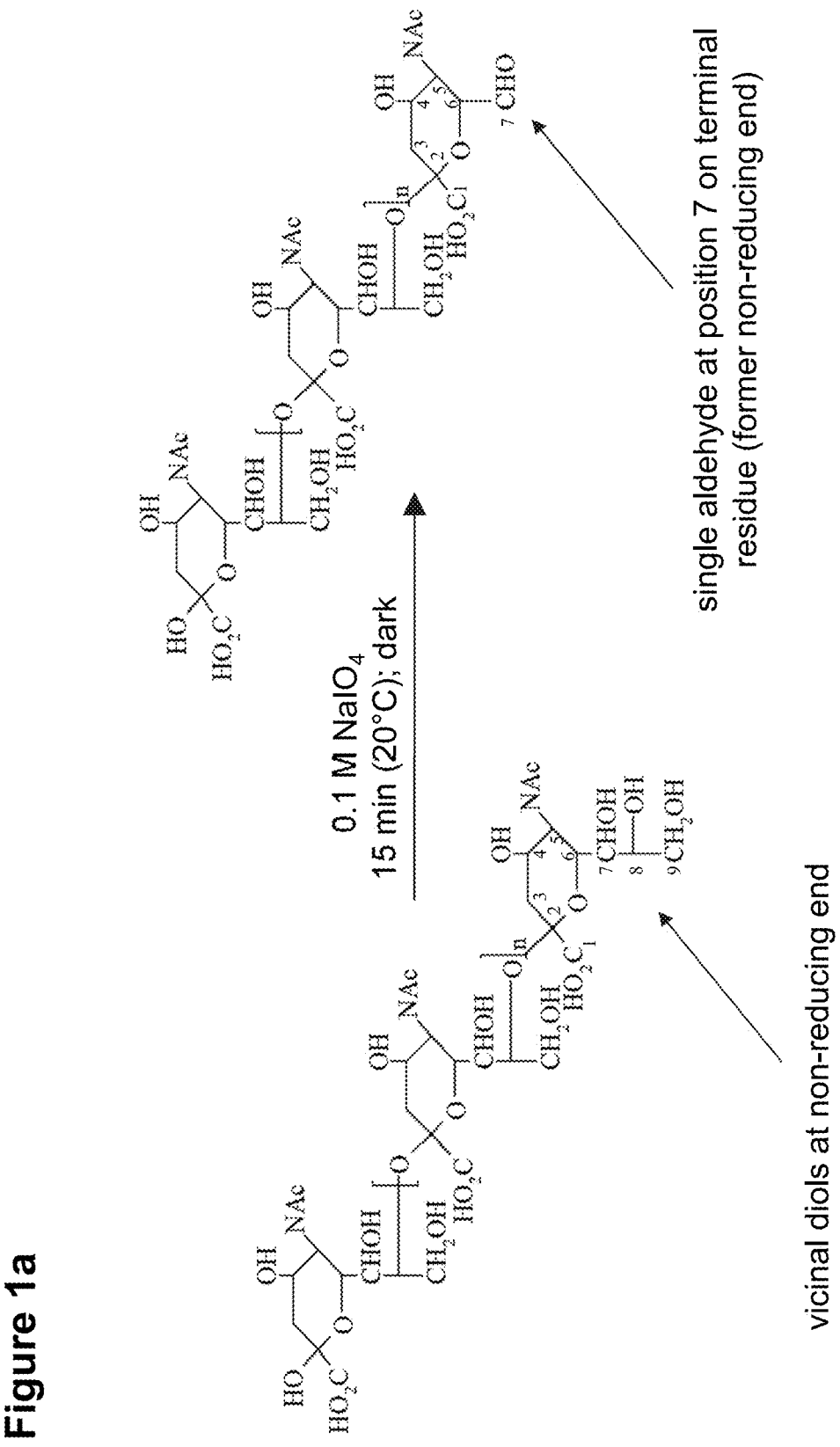
FIG. 1a is a reaction scheme showing the prior art activation of the non-reducing sialic acid terminal unit.

Ammonium carbonate, ethylene glycol, polyethylene glycol (8 KDa), sodium cyanoborohydride (>98% pure), sodium meta-periodate and molecular weight markers were obtained from Sigma Chemical Laboratory, UK. The colominic acid used, linear .alpha.-(2→8)-linked $E.$ $coli$ K1 polysialic acids (22.7 kDa average, high polydispersity 1.34, 39 kDa p.d. 1.4; 11 kDa, p.d. 1.27) was from Camida, Ireland, radioactive iodide ($Na^{125}I$) was purchased from Amersham, UK. Other materials included 2,4 dinitrophenyl hydrazine (Aldrich Chemical Company, UK), dialysis tubing (3.5 KDa and 10 KDa cut off limits; Medicell International Limited, UK), Sepharose SP HiTrap, PD-10 columns (Pharmacia, UK), Tris-glycine polyacrylamide gels (4-20% and 16%), Tris-glycine sodium dodecylsulphate running buffer and loading buffer (Novex, UK). Deionised water was obtained from an Elgastat Option 4 water purification unit (Elga Limited, UK). All reagents used were of analytical grade. A plate reader (Dynex Technologies, UK) was used for spectrophotometric determinations in protein or CA assays. CD 1 outbred mice (8-9 weeks old; 29-35 g body weight) were purchased from Charles River (UK) and acclimatized for at least one week prior to their use Methods Protein and Colominic Acid Determination Quantitative estimation of polysialic acids (as sialic acid) with the resorcinol reagent was carried out by the resorcinol method [Svennerholm, 1957] as described elsewhere [Gregoriadis et al., 1993; Fernandes and Gregoriadis, 1996, 1997]. Fab (protein) was measured by the BCA colorimetric method.

Reference Example 1

Covalent PSA-protein conjugates generated by reductive amination with sodium cyanoborohydride using the natural form of polysialic acid (colominic acid, CA) from $E.$ $coli$, via its weakly reactive reducing end. CA=colominic acid; CAO=oxidised colominic acid as in Fernandes and Gregoriadis, 1996; Jain, et al., 2003. Sodium cyanoborohydride ($NaCNBH_3$) was used at a concentration of 4 mg $ml^{-1}$.

The results are shown in Table 1. The molar ratios in column 1 are the ratio of starting CA(O) to protein. (n=3, ±standard deviation).

TABLE 1

| Preparation | Degree of modification with CA molar ratio (CA:protein) |
| --- | --- |
| Catalase + CAO + $NaCNBH_3$ (10:1) | 0.77 ± 0.16 |
| Catalase + CAO + $NaCNBH_3$ (50:1) | 2.59 ± 0.08 |
| Catalase + CA + $NaCNBH_3$ (50:1) | 0.55 ± 0.05 |
| Catalase + CA (50:1) | 0.65 ± 0.04 |
| Insulin + CAO + $NaCNBH_3$ (25:1) | 1.60 ± 14 |
| Insulin + CAO + $NaCNBH_3$ (50:1) | 1.65 ± 0.14 |
| Insulin + CAO + $NaCNBH_3$ (100:1) | 1.74 ± 0.012 |
| Insulin + CA + $NaCNBH_3$ (25:1) | 0.20 ± 0.02 |
| Insulin + CA + $NaCNBH_3$ (50:1) | 0.21 ± 0.04 |
| Insulin + CA + $NaCNBH_3$ (100:1) | 0.24 ± 0.06 |

Example 1

Preparation of Monofunctional Polysialic Acid

1a Activation of Colominic Acid

Freshly prepared 0.1 M sodium metaperiodate ($NaIO_4$) solution was mixed with CA (100 mg CA/ml $NaIO_4$) at 20° C. and the reaction mixture was stirred magnetically for 15 min in the dark. A two-fold volume of ethylene glycol was then added to the reaction mixture to expend excess $NaIO_4$ and the mixture left to stir at 20° C. for a further 30 min. The oxidised colominic acid was dialysed (3.5 KDa molecular weight cut off dialysis tubing) extensively (24 h) against a 0.01% ammonium carbonate buffer (pH 7.4) at 4° C. Ultrafiltration (over molecular weight cut off 3.5 kDa) was used to concentrate the CAO solution from the dialysis tubing. Following concentration to required volume, the filterate was lyophilized and stored at −40° C. until further use.

1b Reduction of Colominic Acid

Oxidised colominic acid (CAO; 22.7 kDa) was reduced in presence of sodium borohydride. Freshly prepared 0.15 mM sodium borohydride ($NaBH_4$; in 0.1M NaOH diluted to pH 8-8.5 by diluting with dilute $H_2SO_4$ solution) was mixed with CAO (100 mg CA/ml) at 20° C. and the reaction mixture was stirred for up to 2 h in the dark. The pH was brought down to 7 by the completion of the reaction. The oxidised/reduced colominic acid (CAOR) was dialysed (3.5 KDa molecular weight cut dialysis tubing) against 0.01% ammonium carbonate buffer pH (7) at 4° C. Ultracentrifugation was used to concentrate the CAOR solution from the dialysis tubing. The filtrate was lyophilized and stored at 4° C. until further required. The determination of any aldehyde content was determined as described under 'determination of CA oxidation'.

1c Reoxidation of CA

After confirmation of no aldehyde content the oxidised/reduced colominic acid (CAOR) was again oxidised as reported under activation of colominic acid except CAOR was incubated with periodate solution for longer time (up to 1 h). The degree of oxidation in the CAORO product was measured on lyophilized powder obtained from this stage as well.

1d Determination of the Oxidation State of CA and Derivatives

Qualitative estimation of the degree of colominic acid oxidation was carried out with 2,4 dinitrophenylhydrazine (2,4-DNPH), which yields sparingly soluble 2,4 dinitrophenyl-hydrazones on interaction with carbonyl compounds.

Non-oxidised (CA), oxidised (CAO), reduced (CAOR) and re-oxidised (CAORO) (5 mg each), were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949] based on the reduction of ferricyanide ions in alkaline solution to ferric ferrocyanide (Persian blue), which is then measured at 630 nm. In this instance, glucose was used as a standard.

1e Gel Permeation Chromatography

Colominic acid samples (CA, CAO, CAOR and CAORO) were dissolved in $NaNO_3$ (0.2M), $CH_3CN$ (10%; 5 mg/ml) and were chromatographed on over 2×$GMPW_{XL}$ columns with detection by refractive index (GPC system: VE1121 GPC solvent pump, VE3580 RI detector and collation with Trisec 3 software (Viscotek Europe Ltd). Samples (5 mg/ml) were filtered over 0.45 μm nylon membrane and run at 0.7 cm/min with 0.2M $NaNO_3$ and $CH_3CN$ (10%) as the mobile phase.

Results

Colominic acid (CA), a polysialic acid, is a linear alpha-2,8-linked homopolymer of N-acetylneuraminic acid (Neu5Ac) residues (FIG. 1a). Periodate, however, is a powerful oxidizing agent and although selective [Fleury and Lange, 1932] for carbohydrates containing hydroxyl groups on adjacent carbon atoms, it can cause time-dependent cleavage to the internal Neu5Ac residues. Therefore, in the present work exposure of colominic acids to oxidation was limited to 15-60 min using 100 mM periodate at room temperature [Lifely et. al., 1981]. Moreover, as periodate decomposes on exposure to light to produce more reactive species [Dyer, 1956], reaction mixtures were kept in the dark. The integrity of the internal alpha-2,8 linked Neu5Ac residues post periodate and borohydride treatment was analysed by gel permeation chromatography and the chromatographs obtained for the oxidised (CAO), oxidised reduced (CAOR), double oxidised (CAORO) materials were compared with that of native CA. It was found (FIG. 6) that oxidized (15 minutes) (CAO) (6b), reduced (CAOR) (6c), double oxidised (1 hr) (CAORO) (6d) and native (6a) CA exhibit almost identical elution profiles, with no evidence that the successive oxidation and reduction steps give rise to significant fragmentation of the polymer chain. The small peaks are indicative of buffer salts.

Quantitative measurement of the oxidation state of CA was performed by ferricyanide ion reduction in alkaline solution to ferrocyanide (Prussian Blue) [Park and Johnson, 1949] using glucose as a standard [results are shown in table 2]. Table 2 shows that the oxidized colominic acid was found to have a greater than stoichiometric (>100%) amount of reducing agent, i.e. 112 mol % of apparent aldehyde content comprising the combined reducing power of the reducing end hemiketal and the introduced aldehyde (at the other end). No reactivity was seen in CAOR demonstrating that the neutralisation of both the aldehyde and the hemiketal of CAO had been successfully accomplished by borohydride reduction. After the second cycle of periodate oxidation, the aldehyde content of the polymer was restored to 95% in CAORO (within experimental error of 10%) demonstrating the successful introduction of a new aldehyde moiety at the reducing end.

The results of quantitative assay of colominic acid intermediates in the double oxidation process using ferricyanide (Table 2) were consistent with the results of qualitative tests performed with 2,4 dinitrophenylhydrazine which gave a faint yellow precipitate with the native CA, and intense orange colour with the aldehyde containing forms of the polymer, resulting in an intense orange precipitate after ten minutes of reaction at room temperature.

TABLE 2

| CA species | Degree of oxidation |
| --- | --- |
| colominic acid (CA) | 16.1 ± 0.63 |
| colominic acid-oxidised (CAO) | 112.03 ± 4.97 |
| colominic acid-reduced (CAOR) | 0; Not detectable |
| colominic acid-oxidised-reduced-oxidised (CAORO) | 95.47 ± 7.11 |

Degree of oxidation of various colominic acid intermediates in the double oxidation reaction scheme using glucose as a standard (100%, 1 mole of aldehyde per mole of glucose; n = 3 ± s.d).

Example 2

2a Preparation of Fab-Colominic Acid Conjugates

Fab was dissolved in 0.15 M PBS (pH 7.4) and covalently linked to different colominic acids (CA, CAO, CAOR and CAORO) via reductive amination in the presence of sodium cyanoborohydride ($NaCNBH_3$). Colominic acid from each step of the synthesis (starting material and products of each of Examples 1a to c) together with Fab in a CA:Fab molar ratios (100:1) were reacted in 0.15 M PBS (pH 7.4; 2 ml) containing sodium cyanoborohydride (4 mg/ml) in sealed vessels with magnetic stirring at 35±2° C. in an oven. The mixtures was then subjected to ammonium sulphate ($(NH_4)_2SO_4$) precipitation by adding the salt slowly whilst continuously stirring, to achieve 70% w/v saturation. The samples, stirred for 1 h at 4° C., were centrifuged for 15 min (5000×g) and the pellets containing polysialylated Fab suspended in a saturated solution of $(NH_4)_2SO_4$ and centrifuged again for 15 min (5000×g). The precipitates recovered were redissolved in 1 ml 0.15M Na phosphate buffer supplemented with 0.9% NaCl (pH 7.4; PBS) and dialysed extensively (24 h) at 4° C. against the same PBS. The dialysates were then assayed for sialic acid and Fab content and the conjugation yield was expressed in terms of CA:Fab molar ratio. Controls included subjecting the native protein to the conjugation procedure in the presence of non-oxidised CA or in the absence of CA, under the conditions described. Stirring was kept to a minimum to avoid concomitant denaturation of the protein. Polysialylated Fab was further characterised by size exclusion chromatography, ion exchange chromatography and SDS-PAGE.

2b Ion Exchange Chromatography

Zero (control) and 48 h samples (0.5 ml) from the reaction mixtures were subjected to ion exchange chromatography (IEC) on a Sepharose SP cation exchange column (1 ml; flow rate 1 ml/min; binding/washing buffer 50 mM sodium phosphate, pH 4.0; elution buffer, 50 mM sodium phosphate buffer, pH 4.0 containing 1M sodium chloride). The columns were washed, eluted and the eluent fractions were assayed for CA and protein (Fab) content. PD-10 columns were used for desalting samples before applying to column.

2c SDS-Polyacrylamide Gel Electrophoresis

SDS-PAGE (MiniGel, Vertical Gel Unit, model VGT 1, power supply model Consort E132; VWR, UK) was employed to detect changes in the molecular size of Fab upon polysialylation. SDS-PAGE of Fab and its conjugates (with CA, CAO, CAOR and CAORO) of 0 (control) and 48 h samples from the reaction mixtures as well as a process control (non oxidised CA), was carried out using a 4-20% polyacrylamide gel. The samples were calibrated against a wide range of molecular weight markers.

In previous experiments [Jain et. al., 2003; Gregoriadis, 2001] with other proteins it was found that optimal CA:Fab (derived from sheep IgG) molar conjugation yields required a temperature of 35±2° C. in 0.15 M PBS buffer at pH 6-9 for 48 h. The imine (Schiff base) species formed under these conditions between the polymer aldehyde and protein was successfully reduced with $NaCNBH_3$ to form a stable secondary amine [Fernandes and Gregoriadis, 1996; 1997]. Exposure of protein to periodate-oxidised natural CA generates a metastable Schiff's base CA-protein adduct (as reported for the polysialylation of catalase) [Fernandes and Gregoriadis, 1996]. Likewise, in the reaction of oxidised forms of CA with Fab, we first created a metastable Schiff's base adduct, by incubation of the oxidised polymer with Fab for 48 h at 37° C. which was then consolidated by selective reduction (reductive amination) with $NaCNBH_3$ (which reduces the Schiff's base imine structure, but not the aldehyde moiety of the polymer). In order to characterise the protein reactivity of the various CA intermediates of the 'double oxidation method' Fab was subjected to reductive amination in the presence of natural CA (CA), CA oxidized (CAO), CA oxidised-reduced (CAOR) and CA 'double oxidised' (CAORO). For these studies 22.7 kDa PSA was used, at CA:Fab molar ratio of (100:1). After 48 h of incubation in the presence of $NaCNBH_3$, Fab conjugates were isolated from reaction mixtures by precipitation with ammonium sulphate (as described in the "Examples") and the results expressed in terms of CA:Fab molar ratios in the resulting conjugates (Table 3).

TABLE 3

Synthesis of Fab (protein) colominic acid compounds.

| CA species tested | Molar conjugation ratio (CA:Fab) attained |
|---|---|
| colominic acid (CA) | 0.21:1 (weakly reactive) |
| colominic acid-oxidised (CAO) | 2.81:1 (highly reactive) |
| colominic acid-reduced (CAOR) | not detectable (reactivity destroyed) |
| colominic acid-oxidised-reduced-oxidised (CAORO) | 2.50:1 (high reactivity regained) |

It is evident from Table 3 that when natural, non-oxidized CA (in the presence of cyanoborohydride) was used, a significant but low level of conjugation was observed (resulting in a 0.21:1, CA:Fab molar ratio) via reaction with the hemiacetal group of CA at its reducing end.

Figure 7:
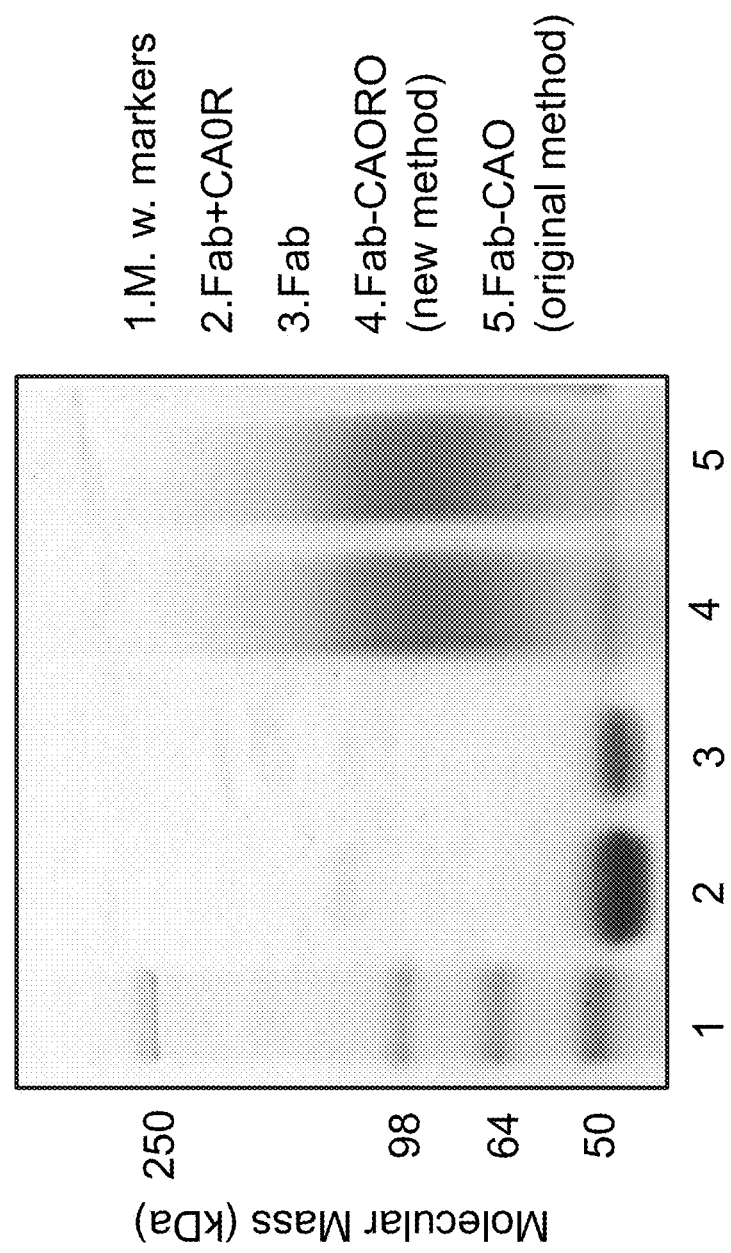
FIG. 7 shows the SDS-PAGE results of example 2.

Formation of the CA-Fab conjugates was further confirmed by the co-precipitation of the two moieties on addition of $(NH_4)_2SO_4$ (CA as such does not precipitate in the presence of the salt). Evidence of conjugation was also confirmed by ion exchange chromatography (IEC, not shown) and polyacrylamide gel electrophoresis (SDS-PAGE; FIG. 7).

For ion-exchange chromatography, polysialylated Fab obtained by $(NH_4)_2SO_4$ precipitation was redissolved in sodium phosphate buffer (50 mM, pH 4.0) and subjected to IEC using a Sepharose SP HiTrap column (cation exchange). In contrast with results indicating complete resolution of CA (in the wash) and Fab (in eluted fractions), both CA and Fab from the 48 h reaction samples co-eluted in the wash fractions, demonstrating the presence of CA-Fab conjugate.

Figure 1B:
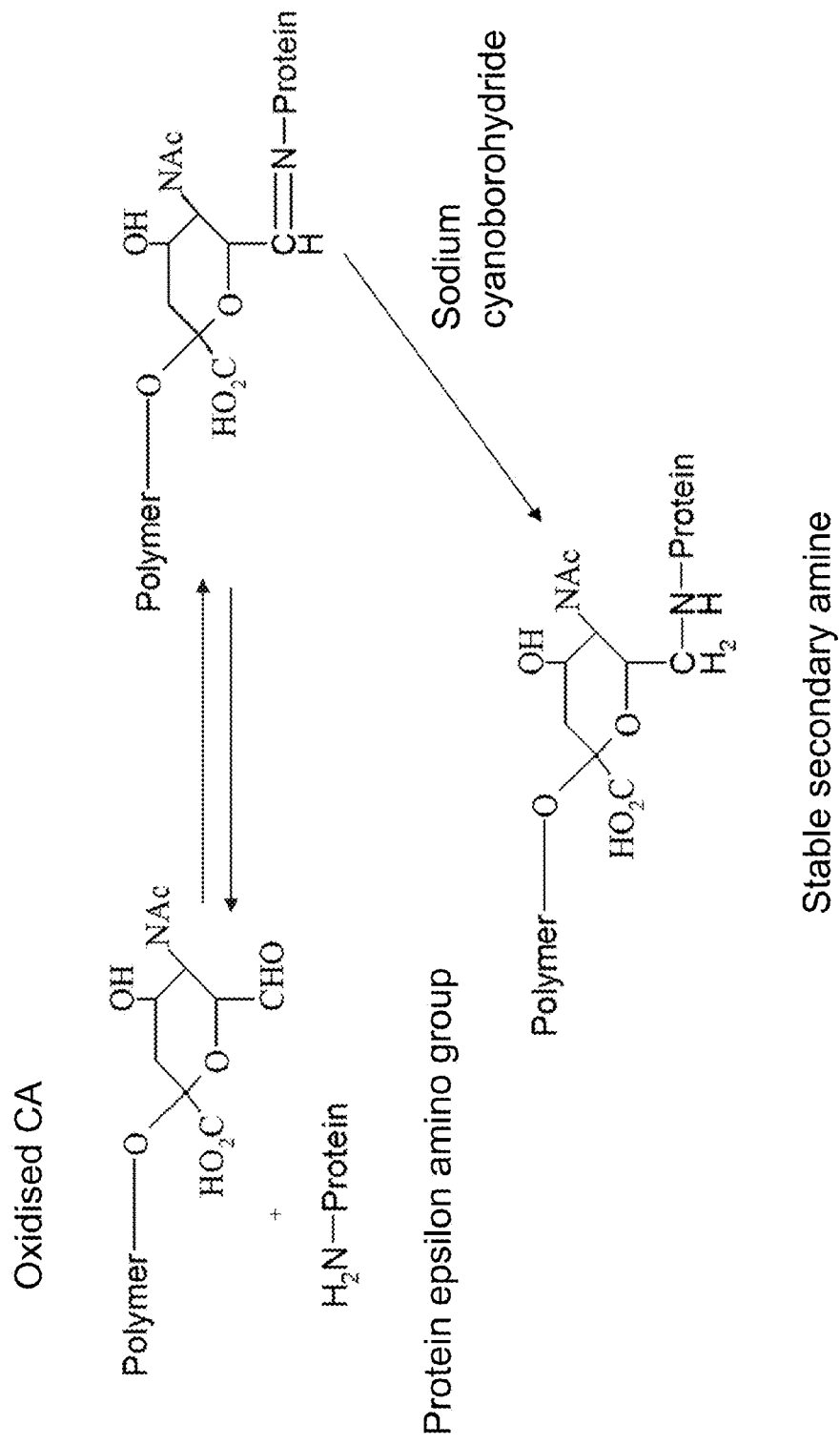
FIG. 1b is a reaction scheme showing the prior art reductive amination of the aldehyde moiety of the product of reaction scheme 1a using a protein-amine moiety.
Figure 2A:
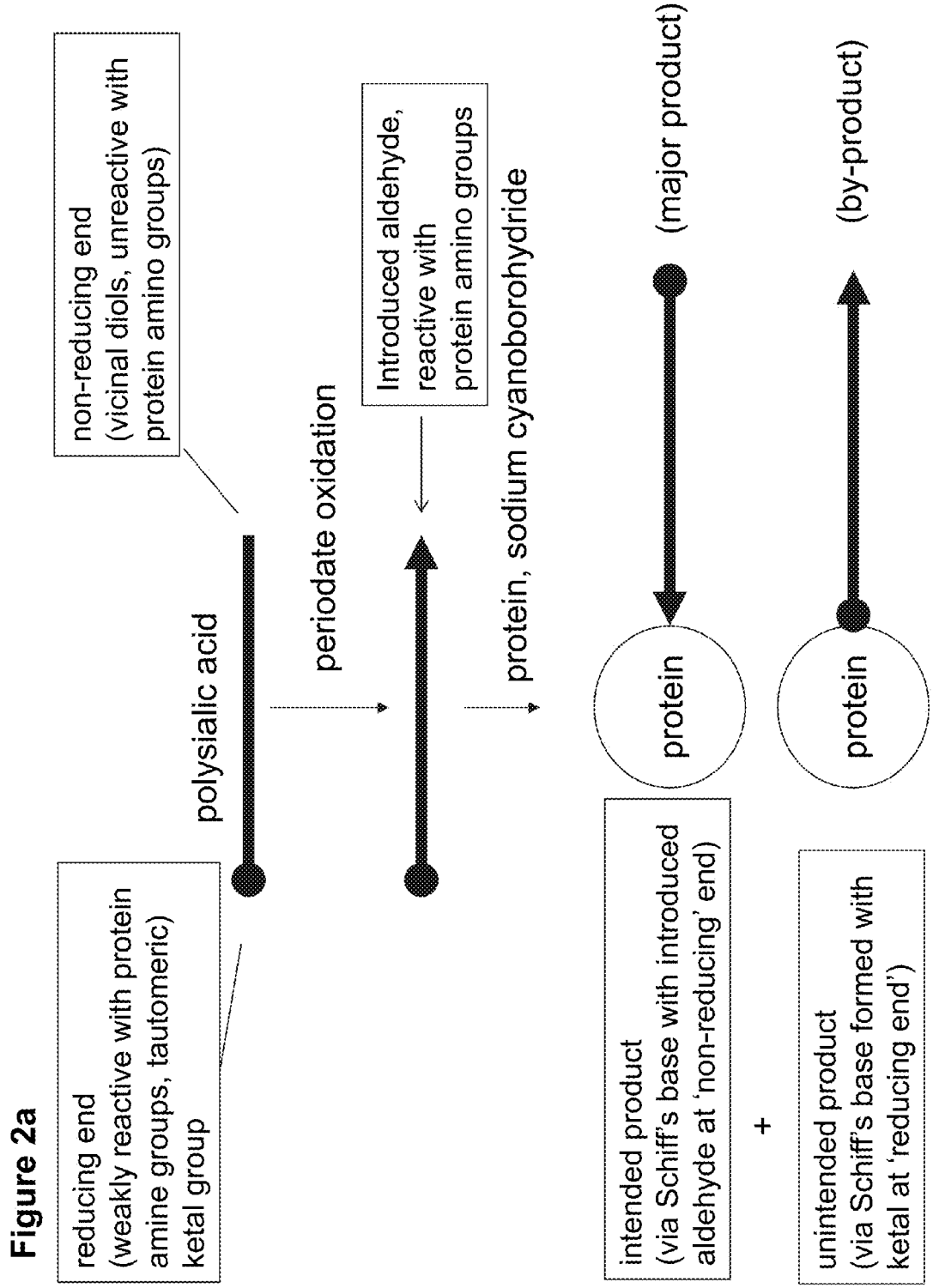
FIG. 2a is a schematic diagram showing the potential side-reactions taking place in the reaction of FIG. 1b involving the reducing terminal.
Figure 2B:
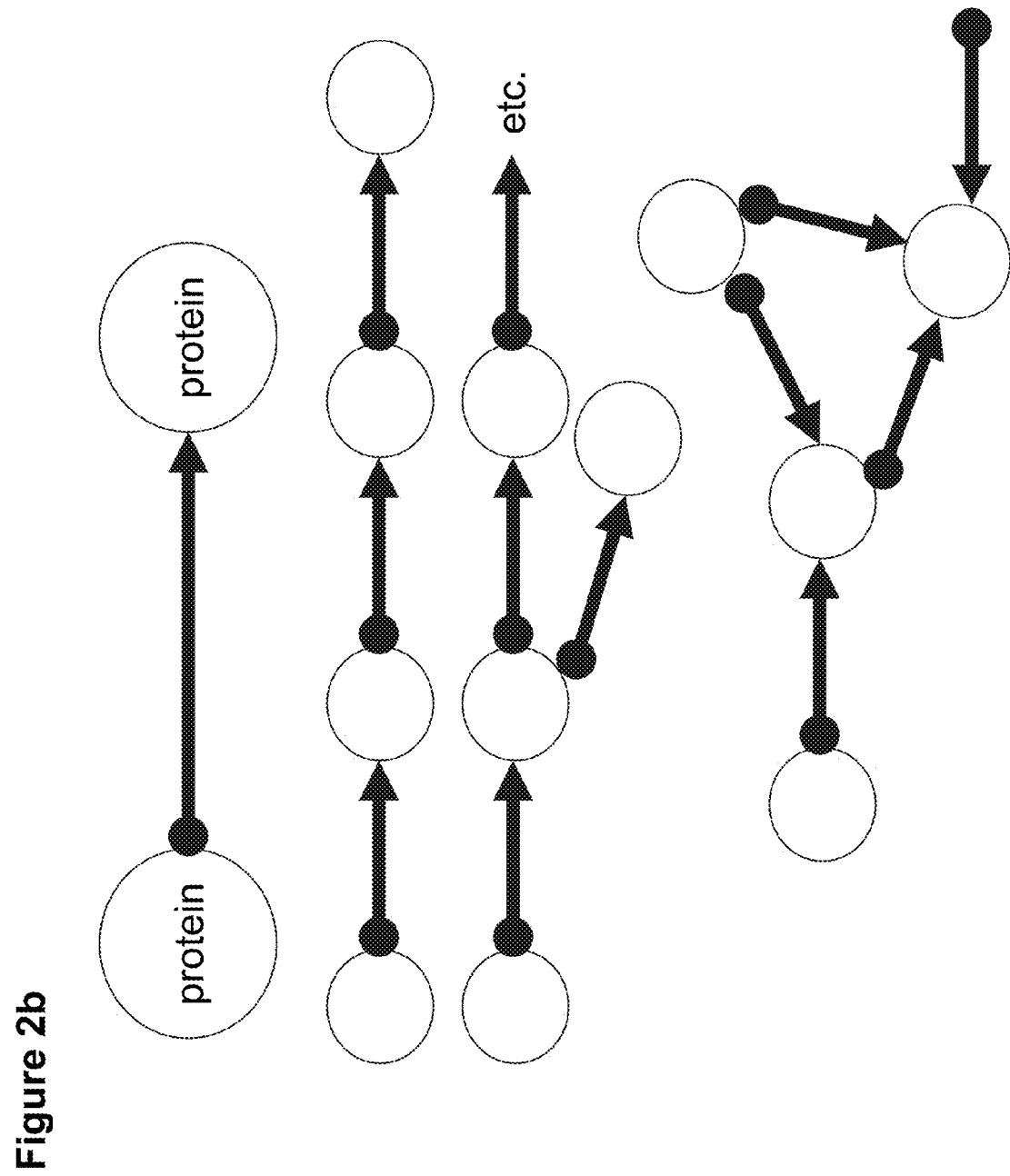
Figure 3:
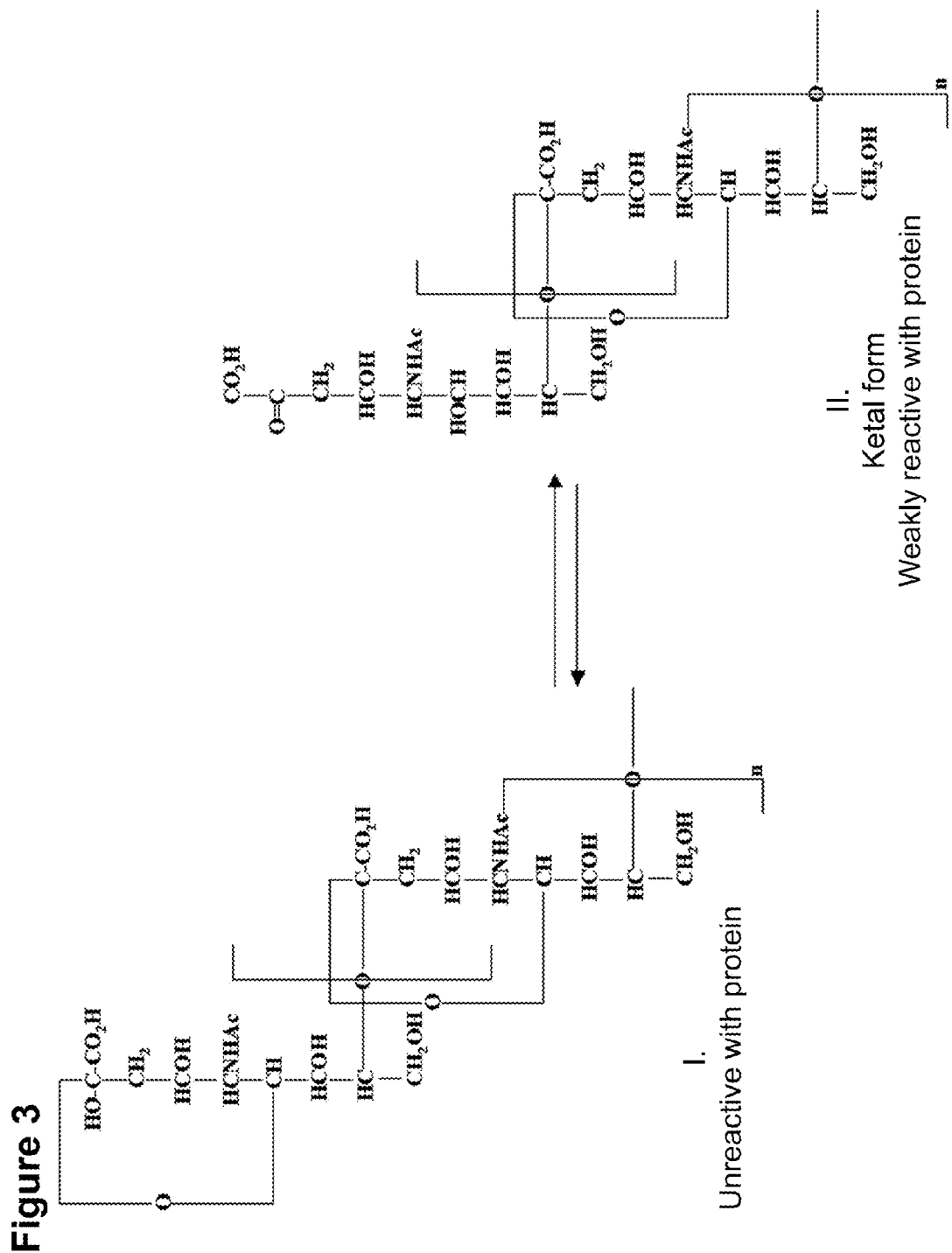
FIG. 3 is a reaction scheme showing the tautomerism between the ketal and ring-closed forms of the reducing terminal sialic acid unit of a PSA.
Figure 4A:
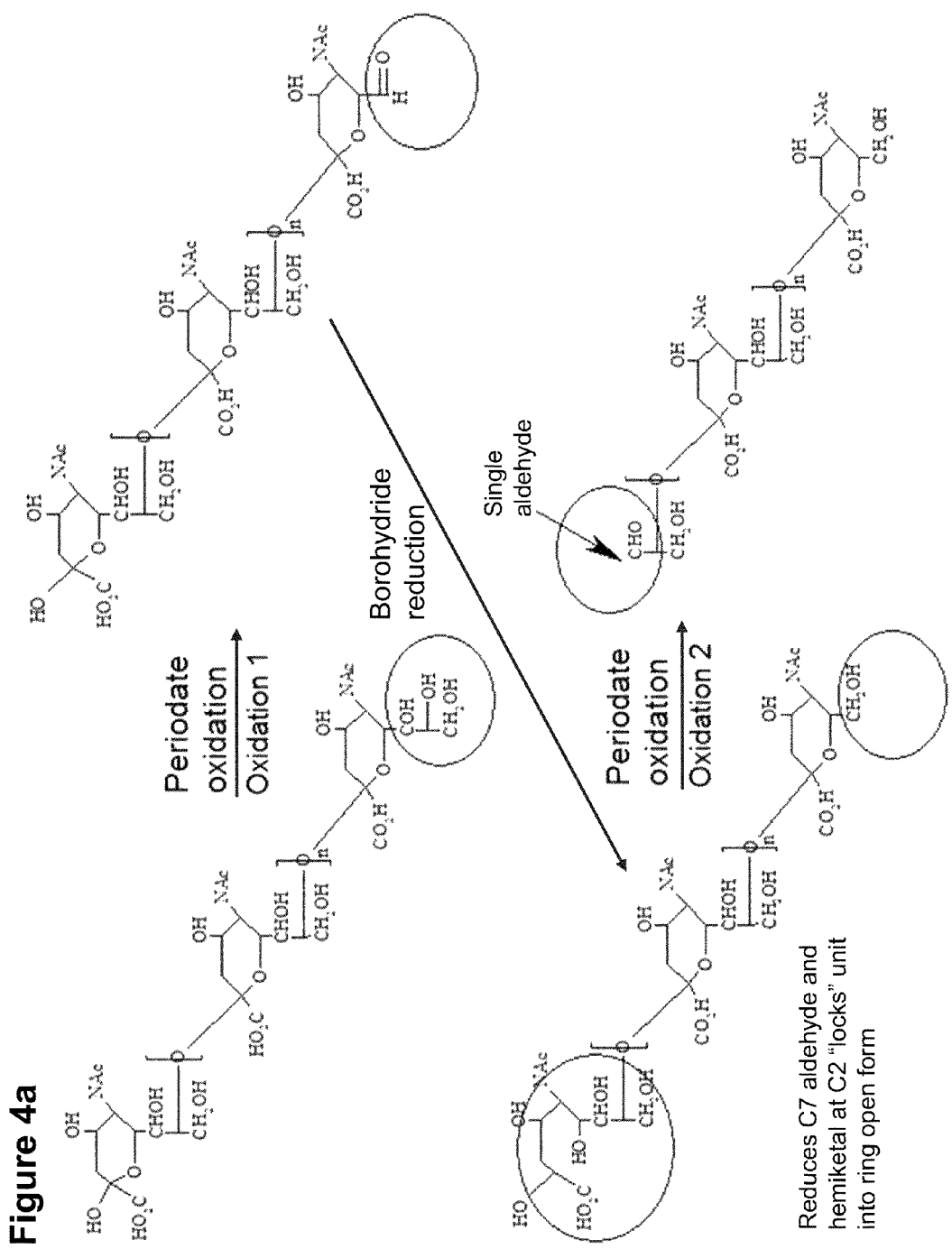
FIG. 4a is a reaction scheme showing the preferred oxidation-reduction oxidation reactions of PSA.
Figure 4B:
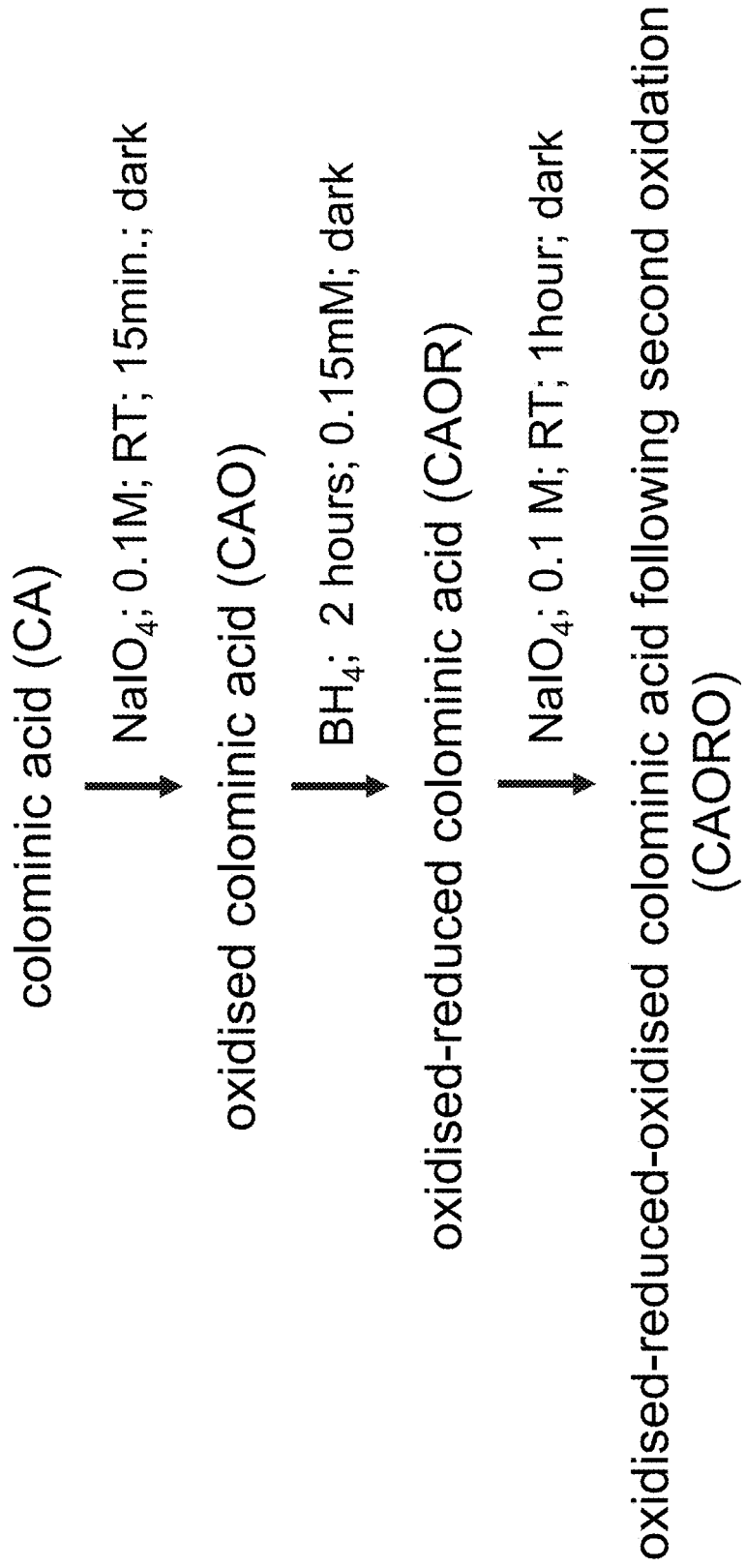
FIG. 4b gives suitable conditions for the steps of the scheme of FIG. 4 and explains abbreviations used for the starting materials, intermediates and end products.
Figure 5:
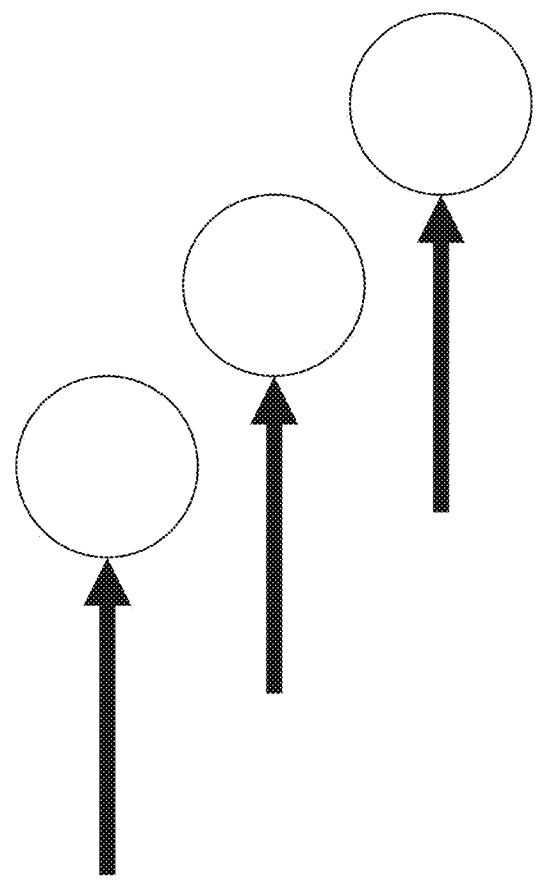
FIG. 5 is a schematic diagram similar to FIG. 2b but shows the products of the reaction of FIG. 4.
Figure 6A:
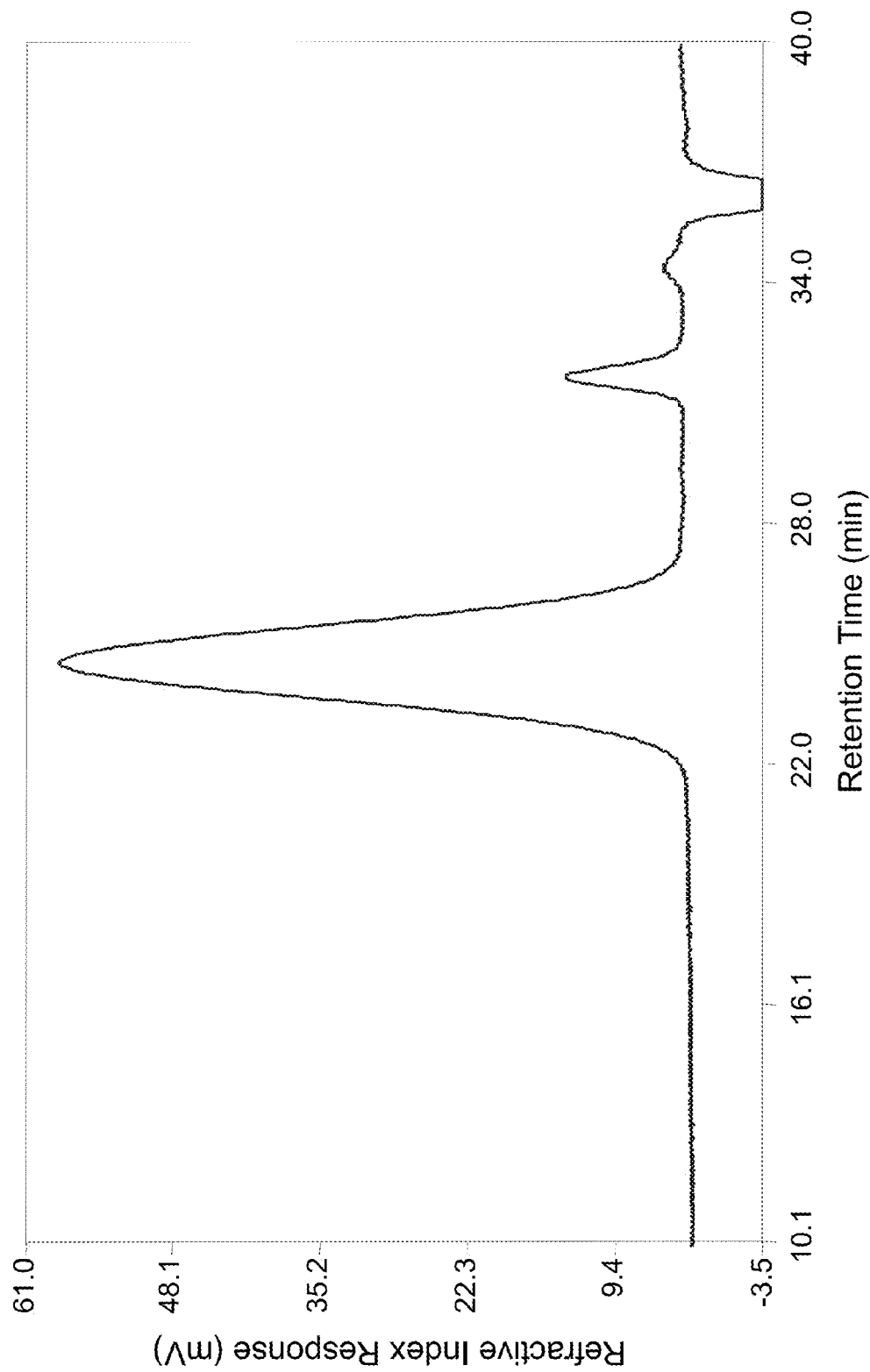
FIGS. 6a-d show the results of the GPC analysis of the products of example 1.
Figure 6B:
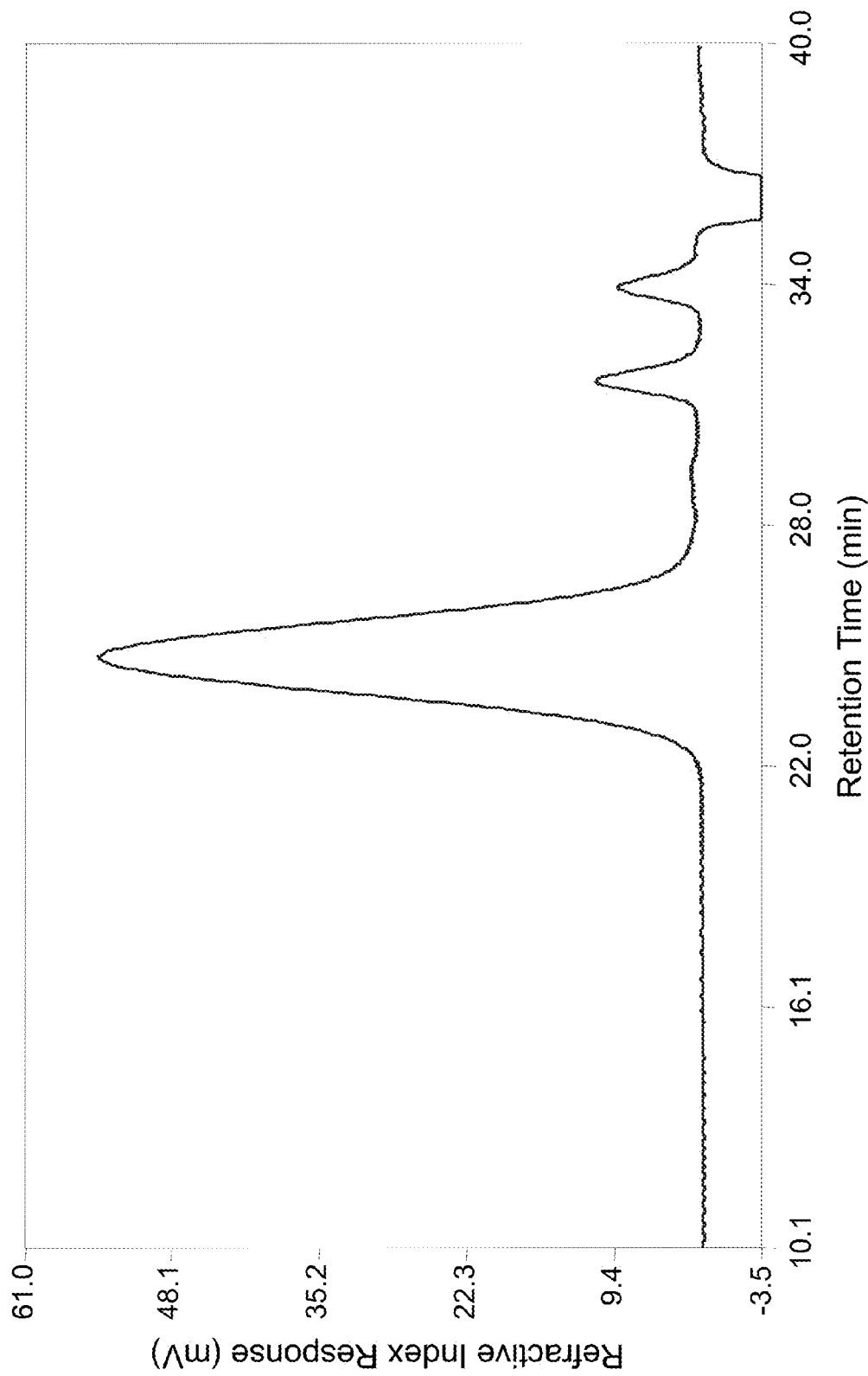
Figure 6C:
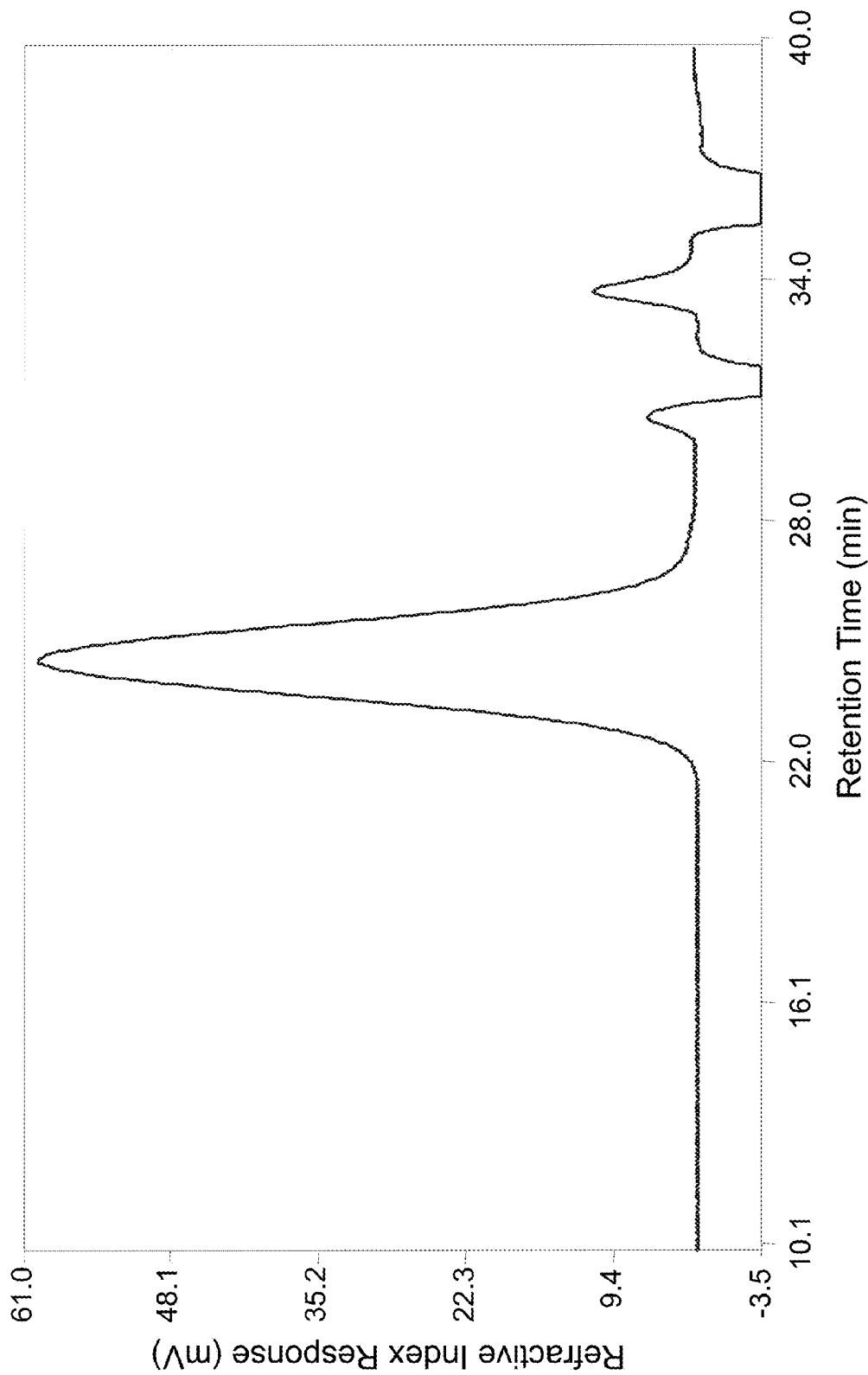
Figure 6D:
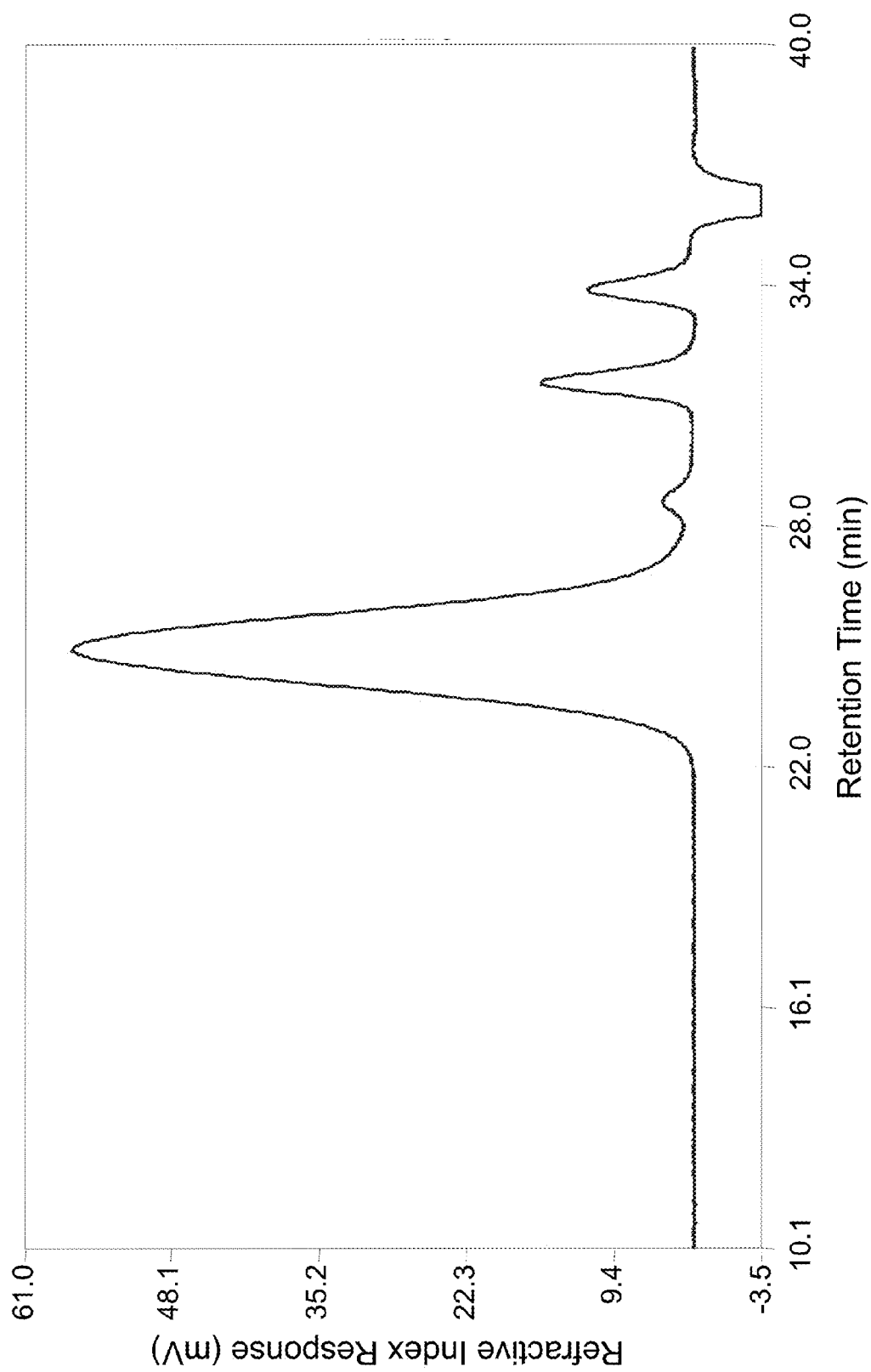

FIG. 7 describes the analysis of the antibody Fab conjugates described above. These data confirm that the molecular weight distributions of the two conjugates are very similar (as expected, since the byproducts obtained from the asymmetrically bifunctional CA make up only a small percentage of the total population of molecules). It is also evident from FIG. 7 that whether Fab conjugates were prepared from asymmetrically bifunctional CA (i.e. periodate oxidised natural CA) or from monofunctional PSA, that conjugates of a wide molecular weight distribution, elevated from the molecular weight of uderivatised Fab control, were created. This is consistent with the known polydispersity of the natural polymer reported in our previous published works. FIG. 7 also confirms that reductive amination with monofunctional CA gives rise to an Fab conjugate with comparable yield to that of the earlier method based on periodate oxidised natural CA (described in FIG. 1). It is also evident from FIG. 7 that only trace amounts of underivatised Fab remained in each conjugate sample. The trace amounts of remaining Fab were removed from these conjugates by ion exchange chromatography prior to in vivo studies (Example 3 below).

Example 3

In Vivo Studies

Samples of sheep IgG Fab fragment or conjugates with CAO or CAORO were radiolabelled with $I^{125}$ as follows:

10% by volume of each of these samples was removed (about 100 μl) and placed into fresh IODO-gen tubes. A 20 μl sample of PBS containing 200 mCi of $^{125}I$ (as NaI) was added to the protein or conjugate and the tubes were capped and allowed to incubate at room temperature for 10 min. The contents of the tubes were then transferred to 500 μl centrifugal filters (3.5 kDa m. w. cut off) and the samples spun at 6,500 rpm in a microcentrifuge. The eluent was discarded and the volume in the retentate (above the membrane) made up to 500 μl. This process was repeated a further 5 times after which the radioactivity above (protein) and below (free iodine) the membrane for a 5 μl sample was assessed using a Packard Cobra Gamma counter. If the counts due to free $^{125}I$ were less than 5% of those in the conjugated fraction, no further purification was carried out. If the free $^{125}I$ was >5% the purification cycle was repeated and the samples re-assessed.

CD1 mice (29-35 g body weight) were dosed with 40 μg (100 μl volume in PBS) of protein per mouse (about 1.6 mg/kg) by the i.v. route (tail vein) as a single injection and 50 μl samples of blood were then taken (using heparinised graduated capillaries) at time intervals from a different tail vein and added into 500 μl PBS. The last bleed recorded was a total bleed in order to allow sufficient counts. Samples were then centrifuged at 3000 rpm for 10 minutes and recorded supernatant removed and placed in gamma counter tubes. Samples were counted along with representative samples of the injected protein in a Packard Cobra II auto gamma counter. Recorded counts were expressed as a percentage of the original dose injected.

Figure 8:
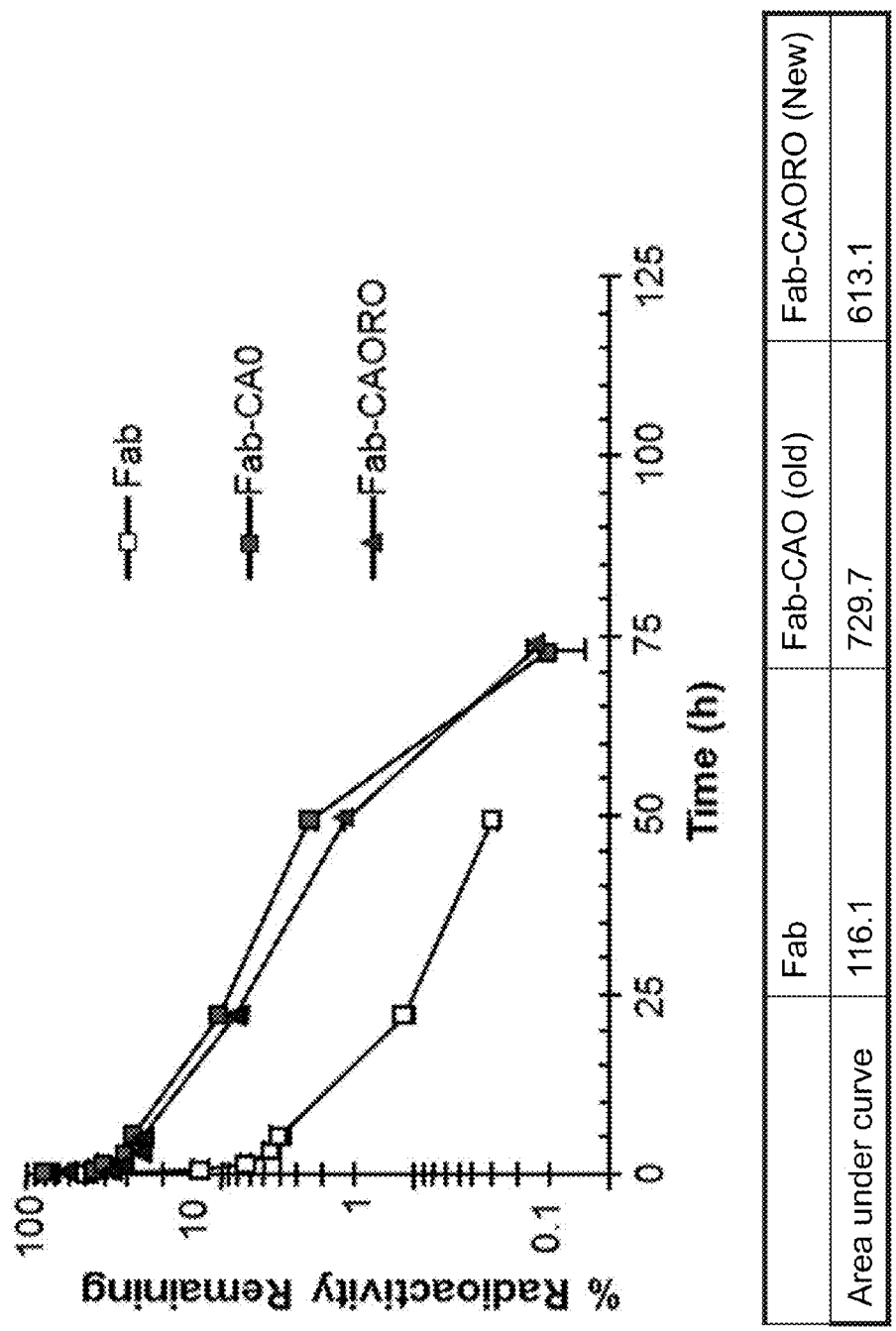
FIG. 8 shows the pharmacokinetics of the circulation half-life of the conjugates tested in vivo in mice in example 3.

Samples of radio-iodinated Fab, and CAO and CAORO Fab conjugates, and injected intravenously into mice to monitor half-life in the blood circulation. FIG. 8 shows the pharmacokinetics of native Fab Vs Fab-colominic acid conjugates prepared by the original method (using CAO) and by the new double-oxidation method (using CAORO). These results demonstrate that CAO-Fab and CAORO-Fab gave rise to marked and significantly longer residence times in the circulation, than was the case for underivatised Fab, giving rise to increases of 6.28 fold and 5.28 fold (respectively) in AUC values compared to native Fab.

Example 4

Synthesis of Maleimide Conjugate

The CAORO synthesised in Example 1c above was reacted with 5 molar equivalents of N-[β-maleimidopropionic acid] hydrazide in 0.1M sodium acetate for 2 h at 37° C. The product hydrazone was precipitated in ethanol, resuspended in sodium acetate and precipitated again in ethanol, redissolved in water and freeze-dried. The product is useful for site-specific conjugation to the thiol groups of cysteine moieties in proteins and peptides.

The monofunctional polysialic acid aldehyde derivative could also be reacted with a linking compound having a hydrazide moiety and a N-maleimide moiety to form a stable hydrazone having an active maleimide functionality useful for reacting with a thiol group.

Reference Example 2

Fractionation of Colominic Acid by Ion Exchange Chromatography (CA, 22.7 KDa, pd 1.34)

Reference Example 2.1

Fractionation at Large Scale

An XK50 column (Amersham Biosciences, UK) was packed with 900 ml Sepharose Q FF (Amersham Biosciences) and equilibrated with 3 column volumes of wash buffer (20 mM triethanolamine; pH 7.4) at a flow rate of 50 ml/min. CA (25 grams in 200 ml wash buffer) was loaded on column at 50 ml per minute via a syringe port. This was followed by washing the column with 1.5 column volumes (1350 ml) of washing buffer.

The bound CA was eluted with 1.5 column volumes of different elution buffers (Triethanolamine buffer, 20 mM pH 7.4, with 0 mM to 475 mM NaCl in 25 mM NaCl steps) and finally with 1000 mM NaCl in the same buffer to remove all residual CA and other residues (if any).

The samples were concentrated to 20 ml by high pressure ultra filtration over a 5 kDa membrane (Vivascience, UK). These samples were buffer exchanged into deionised water by repeated ultra filtration at 4° C. The samples were analysed for average molecular weight and other parameters by GPC (as reported in example 1e) and native PAGE (stained with alcian blue).

Reference Example 2.2

Fractionation at Smaller Scale

The following samples were fractionated using an identical wash and gradient system on a smaller scale (up to 75 ml matrix; 0.2-3 gram of colominic acid):

Colominic acid (CA, 22.7 kDa, pd 1.34; CA, 39 KDa, pd=1.4), colominic acid-aldehyde (CAO, 22.7 kDa, pd 1.34), monofunctional colominic acid (CAORO, 22.7 kDa; pd 1.34), colominic acid-amine (CA-NH2, 22.7 kDa, pd 1.34), colominic acid maleimide (CAM, as per example 4 and the m.w. of CA produced monitored throughout).

Narrow fractions of CA produced using above procedure were oxidised with 10 mM periodate and analysed by gel permeation chromatography (GPC) and native PAGE for gross alteration to the polymer.

Results

TABLE 4

Ion exchange chromatography of CA22.7:
Scale up (75 ml matrix, 3 g of CA)

| Elution buffers (in 20 mM Triethanolamine buffer + mM NaCl, pH 7.4) | M.W. | Pd | % Population |
|---|---|---|---|
| 325 mM | 12586 | 1.091 | 77.4% |
| 350 mM | 20884 | 1.037 | 3.2% |
| 375 mM | 25542 | 1.014 | 5.0% |
| 400 mM | 28408 | 1.024 | 4.4% |
| 425 mM | * | * | 7.4% |
| 450 mM | 43760 | 1.032 | 2.3% |
| 475 mM | 42921 | 1.096 | 0.2% |

* Not done

Figure 9:
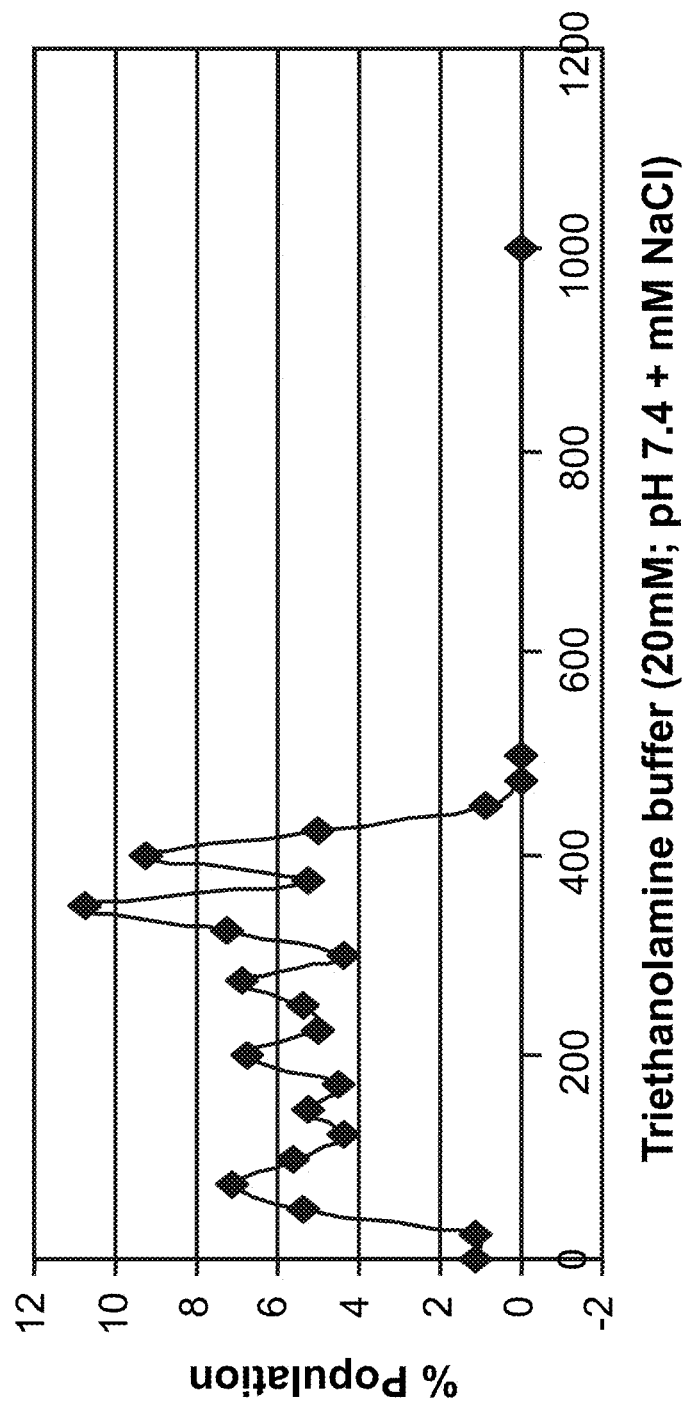
FIG. 9 shows the IEC results for CA22.7 kDa in Reference example 2.
Figure 10:
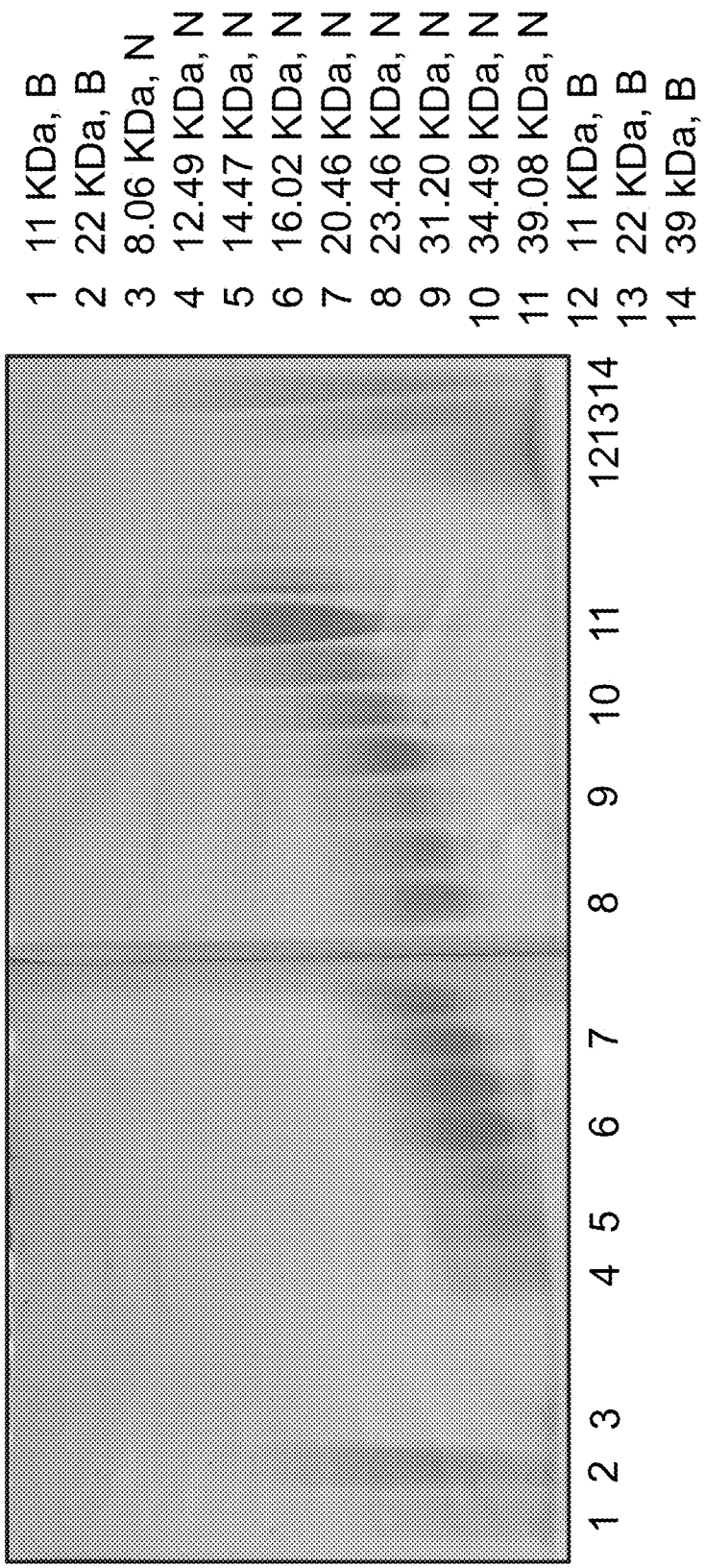
FIG. 10 shows the native PAGE results for CA22.7 kDa Reference Example 2.

Colominic acid and its derivatives (22.7 kDa) were successfully fractionated into various narrow species with a polydispersity less than 1.1 with m.w. averages of up to 46 kDa with different % of populations. FIGS. 9 and 10; Table 4 show the results of separating the 22.7 kDa material at a scale of 75 ml. FIG. 9 is the GPC result and FIG. 10 is a native PAGE.

This process was scalable from 1 ml to 900 ml of matrix with the fractionation profile almost identical at each scale (not all results shown).

Figure 11:
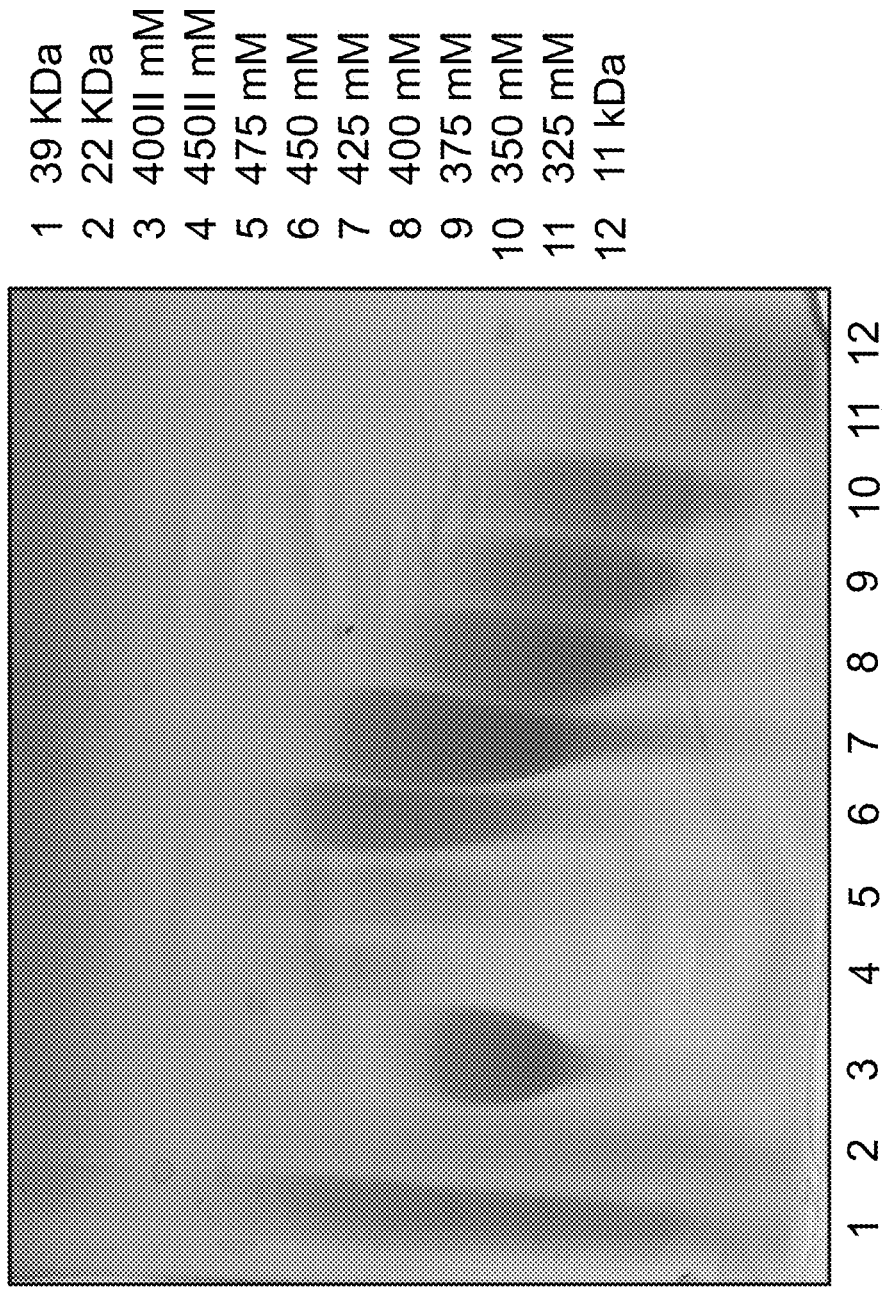
FIG. 11 shows the native PAGE results for several CA materials as supplied and fractions separated as in Reference example 2.2.
Figure 12:
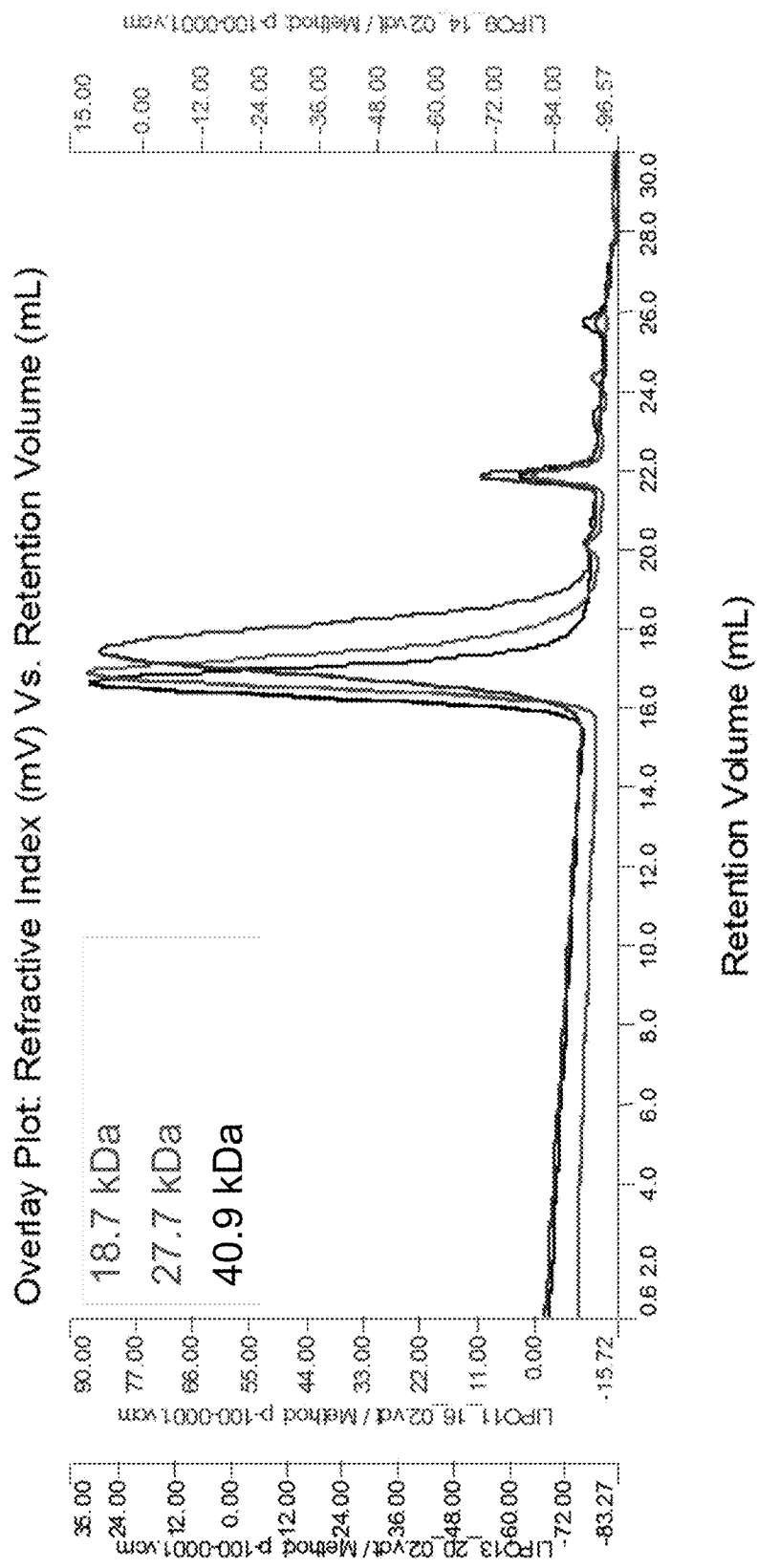
FIG. 12 shows GPC chromatograms for 3 of the fractions of CA separated as in Reference example 2.2.

The fractionation of larger polymer (CA, 39 kDa, pd 1.4) produced species up to 90 kDa. This process can successfully be used for the fractionation of even large batches of the polymer. FIG. 11 shows the native PAGE results for the 3 CA samples as supplied and for fractions separated by ion-exchange analysed as in Table 4. The PAGE results show that the ion exchange fractions are narrowly dispersed. This is consistent with the GPC data shown in FIG. 12 which shows the results for 3 of the fractions separated from the 22.7 kDa CA. The retention volumes are shown in Table 5.

TABLE 5

| Sample | M.W. | Mn | PD |
|---|---|---|---|
| 1 | 18727 | 15016 | 1.25 |
| 2 | 27677 | 25095 | 1.10 |
| 3 | 40950 | 40279 | 1.02 |

The 22.7 kDa material is separated on a larger scale. Using GPC the fractions from ion exchange are analysed. The following fractions shown in Table 6 (see FIG. 18) were recovered.

Figure 13:
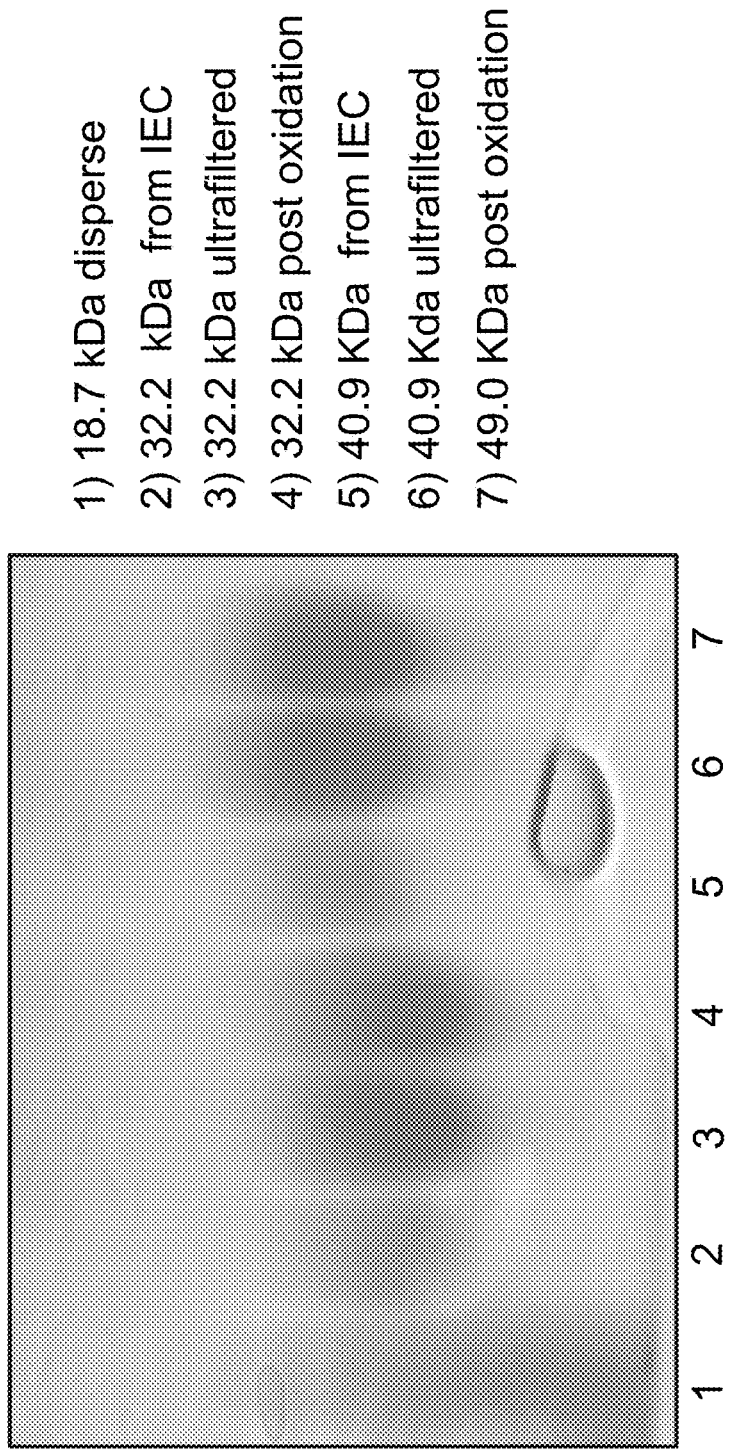
FIG. 13 shows native PAGE for two of the samples used in FIG. 12 and other CA and CAO samples as described in Reference example 2.2.

All narrow fractions were successfully oxidised with 10 mM periodate and samples taken from different stages of the production process and analysed by GPC and native PAGE showed no change in the molecular weight and polydispersity The data for some of the samples are shown in FIG. 13.

2.3 Precipitation of Colominic Acid

Differential ethanol precipitation was used to precipitate different chain lengths of colominic acid.

Results

Differential ethanol precipitation showed that smaller CAs required more ethanol (EtOH). Broad p.d. 22.7 kDa polymer was precipitated with 70% EtOH giving a yield>80% of product polymer. A concentration of 80% EtOH was required to precipitate>80% of a lower MW 6.5 KDa (pd<1.1). This process also removes any salt contaminating the product.

2.4 Fractionation of Colominic Acid by Filtration

Samples of 22.7 kDa were purified by ultrafiltration over different molecular weight cut off membranes (5, 10, 30, 50, and 100 kDa). In all cases retentate was examined by GPC and native PAGE.

Results

Figure 14:
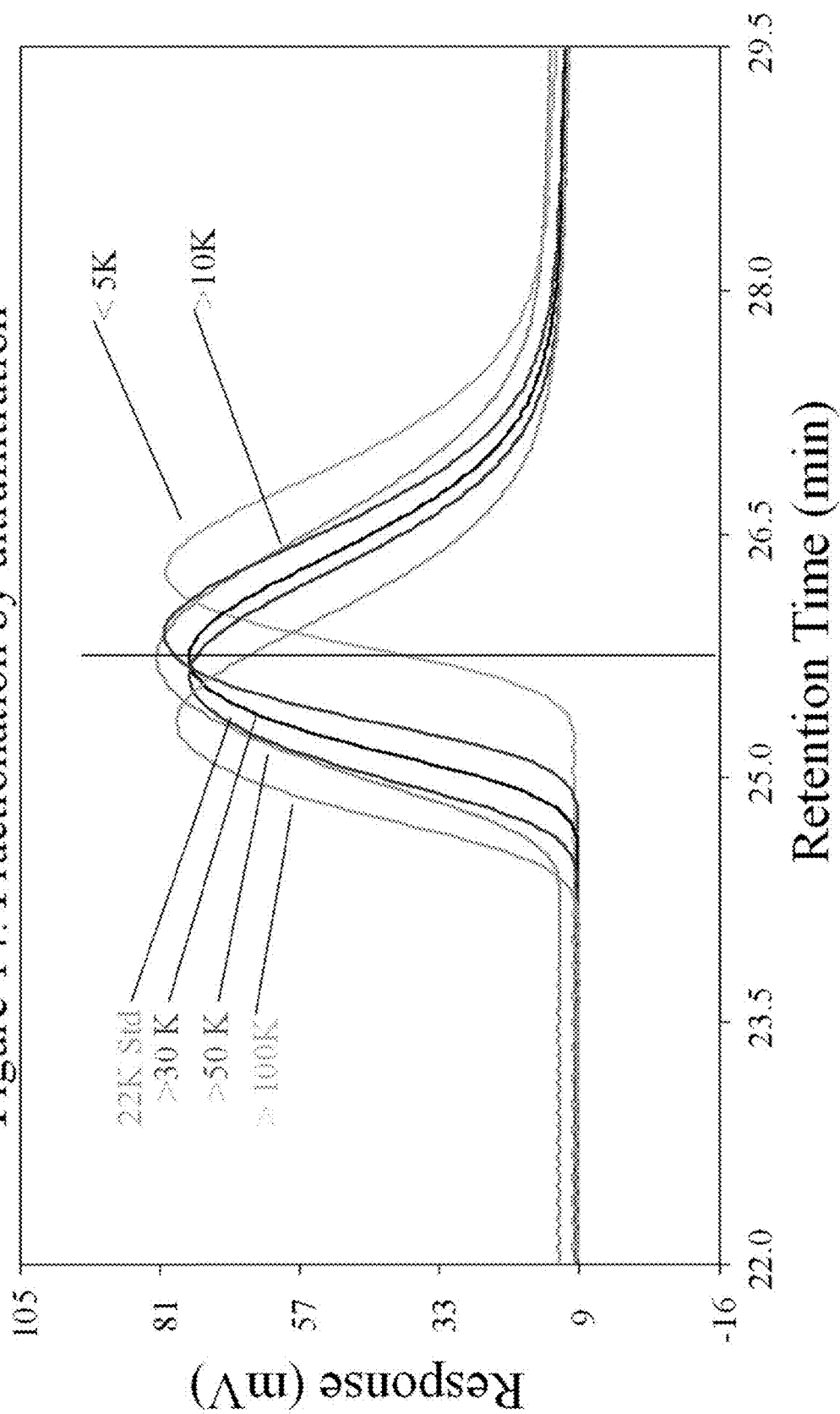
FIG. 14 shows the results of ultrafiltration of the CA 22.7 kDa as described in Reference example 2.4.

Samples of 22.7 kDa were purified by ultrafiltration over different molecular weight cut off membranes showed that there was a decrease in polydispersity of the polymer and a shift towards higher molecular weight with increase in membrane cut off (FIG. 14).

Combined methods and ion pair chromatography can also be for fractionation of the polymers.

Example 5

Synthesis of Growth Hormone (GH)-Colominic Acid Conjugates (Broad and Narrow Dispersed)

Colominic acid-oxidised (CAO; 22.7 kDa)) and narrow dispersed-colominic acid-oxidised (NCAO; 27.7 kDa pd=1.09; 40.9 kDa. pd=1.02) prepared in Reference example 2.2 was used for the preparation of GH conjugates.
Preparation of Growth Hormone-Colominic Acid Conjugates Growth hormone was dissolved in 0.15 M PBS (pH 7.4) and covalently linked to different colominic acids (CAO and NCAO). Different CAs (22.7 kDa, CAO; 27.7 kDa & 40.9 kDa, NCA)) were individually added to GH (2 mg) in a CA:GH molar ratios (12.5:1), sodium cyanoborohydride was added to a final concentration of 4 mg/ml. The reaction mixtures were sealed and stirred magnetically for 24 h at 35±2° C. The mixtures were then subjected to ammonium sulphate (($NH_4$)$_2SO_4$) precipitation by adding the salt slowly whilst continuously stirring, to achieve 70% w/v saturation, stirred for 1 h at 4° C., then spun (5000×g) for 15 min and the pellets resuspended in a saturated solution of ($NH_4$)$_2SO_4$ and spun again for 15 min (5000×g). The precipitates recovered were redissolved in 1 ml PBS pH 7.4 and dialysed extensively (24 h) at 4° C. against the same buffer. Controls included subjecting the native protein to the conjugation procedure in the presence of non-oxidised CA or in the absence of CA. Shaking was kept to a minimum to avoid concomitant denaturation of the protein. Polysialylated GH was characterised by SDS-PAGE. The polysialylated GH was passed through anion exchange chromatography as described in Reference example 2 and the product fractions subjected to SDS PAGE.

Results

Figure 15:
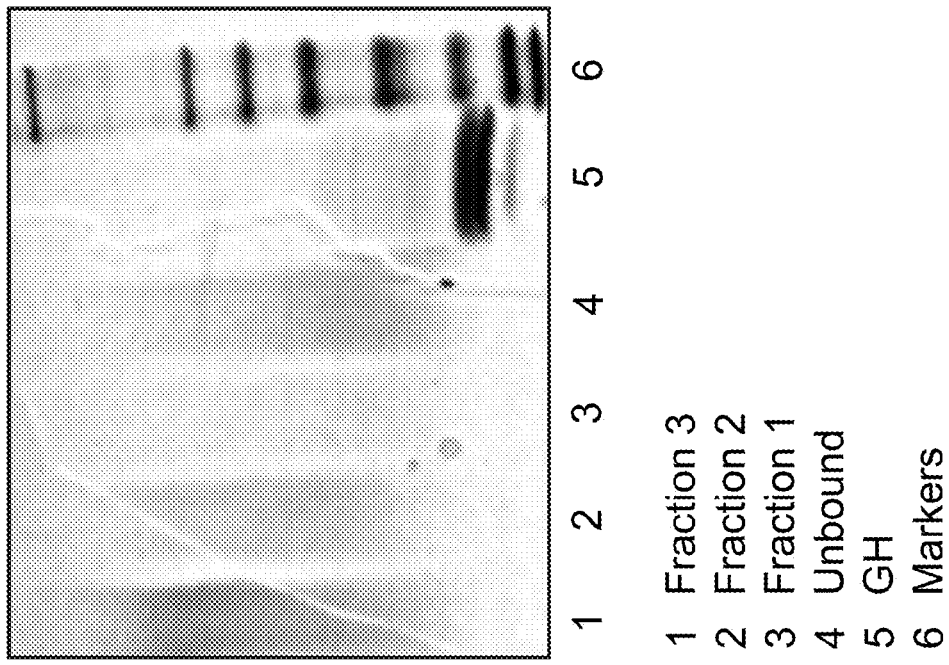
FIG. 15 shows SDS PAGE for Example 5.
Figure 16:
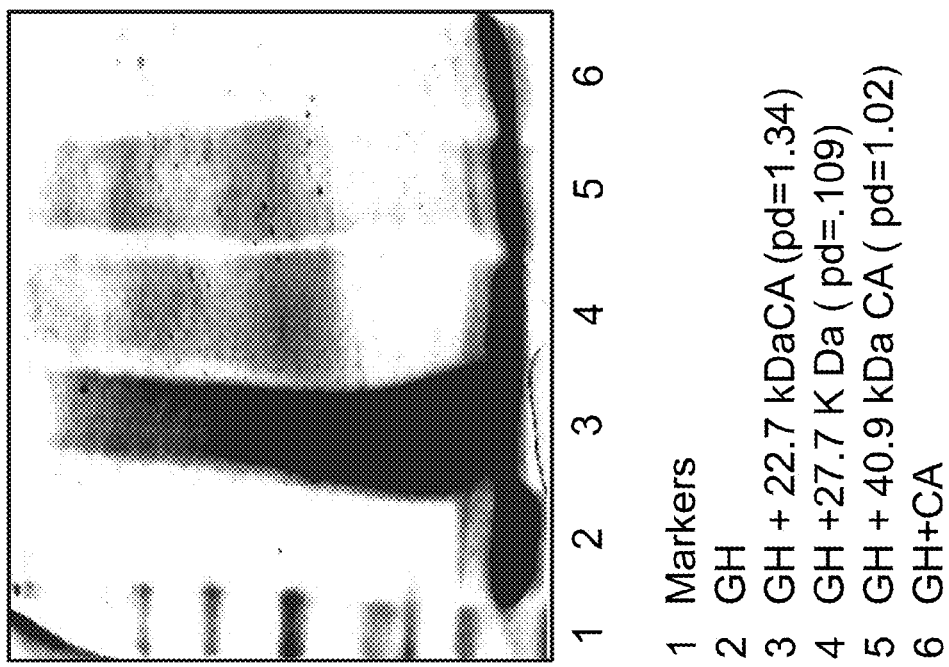
FIG. 16 shows SDS PAGE results for fractionated GH-CA conjugates formed as in Example 5.

The results (FIG. 15) show that in control well (with GH) the migration of the sample is similar to that for fresh GH. In the conjugate lanes there are shifts in the bands which typically indicates an increase in mass indicative of a polysialylated-GH. The band width was significantly narrowed down in case of conjugates with narrow dispersed polymer in comparison to conjugates with broad dispersed polymers. Further, GH conjugates (with broad dispersed polymer) were separated into different species by anion exchange chromatography (FIG. 16).

Example 6

Synthesis of Insulin-Colominic Acid Conjugates

Activated polysialic acid (colominic acid-oxidised (CAO)) and monofunctional polysialic acid (colominic acid-oxidised-reduced-oxidised (CAORO)) prepared in example 1 was used for the preparation of rh-insulin conjugates.
Preparation of Insulin-Colominic Acid Conjugates Insulin was dissolved in a minimum volume of 15 mM HCl followed by dilution with 0.15 M PBS (pH 7.4) and covalently linked to different colominic acids (CA, CAO and monofunctional CAORO). Colominic acid (22.7 kDa) together with insulin (2 mg) in a CA:insulin molar ratios (25:1) were reacted for 48 h in 0.15 M PBS (pH 7.4; 2 ml) containing sodium cyanoborohydride (4 mg/ml) in sealed vessels with magnetic stirring at 35±2° C. in an incubator. The mixtures was then subjected to ammonium sulphate (($NH_4$)$_2SO_4$) precipitation by adding the salt slowly whilst continuously stirring, to achieve 70% w/v saturation. The samples were stirred for 1 h at 4° C., then spun (5000×g) for 15 min and the pellets suspended in a saturated solution of ($NH_4$)$_2SO_4$ and centrifuged again for 15 min (5000×g). The precipitates recovered were redissolved in 1 ml 0.15M Na phosphate buffer supplemented with 0.9% NaCl (pH 7.4; PBS) and dialysed extensively (24 h) at 4° C. against the same PBS. The dialysates were then assayed for sialic acid and protein content and the conjugation yield was expressed in terms of CA:insulin molar ratio (as per example 1). Controls included subjecting the native protein to the conjugation procedure in the presence of non-oxidised CA or in the absence of CA, under the conditions described. Shaking was kept to a minimum to avoid concomitant denaturation of the protein. Polysialylated insulin was further characterised by ion exchange chromatography and SDS-PAGE. Results are expressed in terms of CA:insulin molar ratios in the resulting conjugates (Table 7).

TABLE 7

Synthesis of insulin (protein) colominic acid compounds

| CA species tested | Molar conjugation ratio (CA:insulin) attained |
|---|---|
| colominic acid (CA) | 0.07:1 (weakly reactive) |
| colominic acid-oxidised (CAO) | 1.60:1 (highly reactive) |
| colominic acid-oxidised-reduced-oxidised (CAORO) (monofunctional) | 1.35:1 (high reactivity regained) |

It is evident from Table 7 that when natural, non-oxidized CA (in the presence of cyanoborohydride) was used, a significant but low level of conjugation was observed (resulting in a 0.07:1, CA:insulin molar ratio) via reaction with the hemiacetal group of CA at its reducing end.

Formation of the CA-insulin conjugates was further confirmed by the co-precipitation of the two moieties on addition of ($NH_4$)$_2SO_4$ (CA as such does not precipitate in the presence of the salt). Evidence of conjugation was also confirmed by ion exchange chromatography (IEC) and polyacrylamide gel electrophoresis (SDS-PAGE).

Example 7

In Vivo Studies

Insulin and polysialylated insulin constructs of Example 6 were tested for their ability to reduce blood glucose level in normal female TIO outbred mice (22-24 gram body weight). Animals were divided into groups of five, injected subcutaneously (s.c.) with insulin (0.3 units per mouse in 0.9% sodium chloride or with the same protein equivalence of polysialylated insulin) and glucose levels in blood samples were measured at time intervals using a glucose assay kit (Accu-Chek Advantage, Roche, UK).

Results

Figure 17:
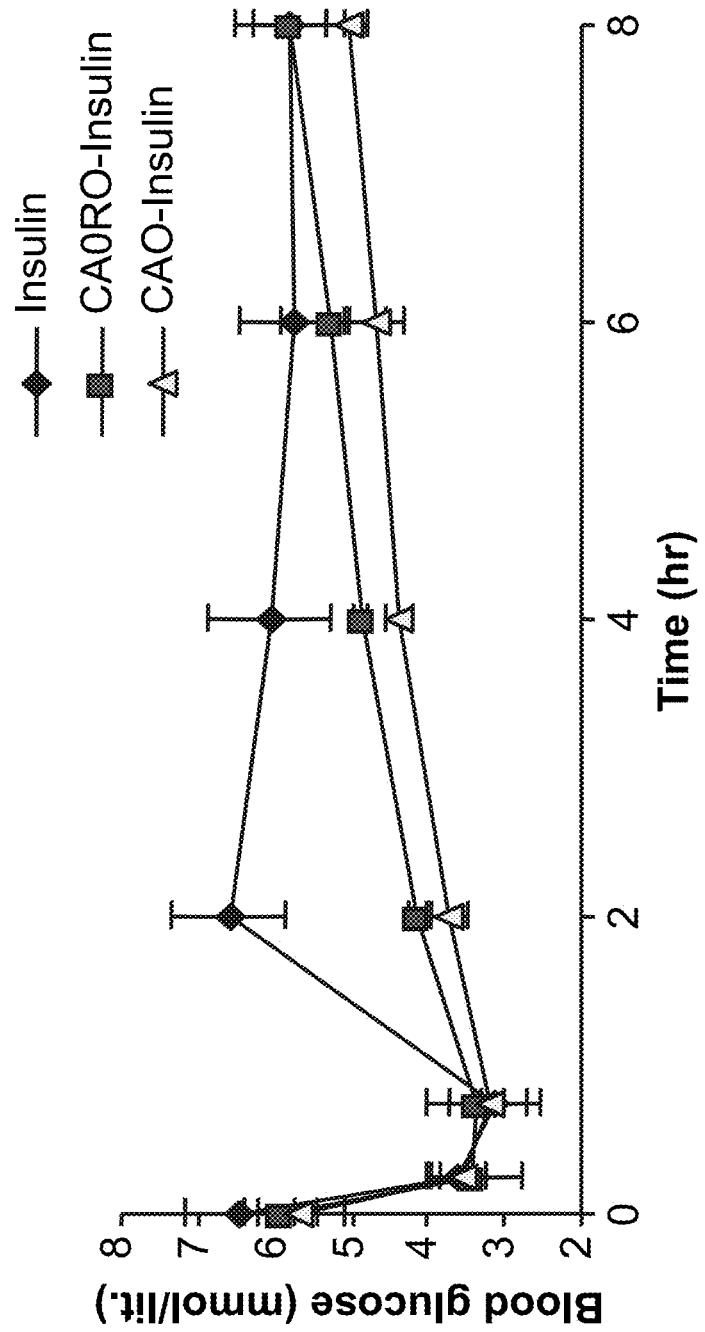
FIG. 17 shows the results of Example 7.

The pharmacological activity of polysialylated insulin constructs was compared with that of intact insulin in normal mice injected subcutaneously and bled at time intervals. The blood glucose levels of the mice for the 3 insulins are shown in FIG. 17. The data points show the average of 5 samples and the error bars are the s.e.m. values. Results in FIG. 17 clearly show that polysialylated insulins (prepared by original method (using CAO) and by the new double-oxidation method (using monofunctional CAORO)) exerted a more prolonged reduction of blood glucose levels. Thus, whereas glucose levels attained nadir values at 0.75 hours to return to normal levels two hours after treatment with intact insulin, glucose levels in mice treated with the polysialylated peptide, although also lowest at 0.75 h, returned to normal values at 6 hours. These results demonstrate that CAO-insulin and CAORO-insulin gave rise to marked and significantly longer residence times in the circulation, than was the case for underivatised insulin, giving rise to increases in area above curve compared to native insulin.

REFERENCES

Bendele, A., Seely, J., Richey, C., Sennello, G., Shopp, G., Renal tubular vacuolation in animals treated with poly-ethylene-glycol conjugated proteins, Toxicological sciences, 42 (1998) 152-157.

Beranova, M., Wasserbauer, R., Vancurova, D., Stifter, M., Ocenaskova, J., Mora, M., Biomaterials, 11 (2000) 521-524. [0164] Brocchini, S., Polymers in medicine: a game of chess. Drug Discovery Today, 8, (2003) 111-112.

Cheng T, Wu, M., Wu, P., Chem, J, Roffer, S R., Accelerated clearance of polyethylene glycol modified proteins by anti-polyethylene glycol IgM. Bioconjugate chemistry, 10 (1999) 520-528.

Cho, J. W. and Troy, F. A., Polysialic acid engineering: Synthesis of polysialylated neoglycosphingolipid by using the polytransferase from neuroinvasive E. coli K1, Proceedings of National Academic Sciences, USA, 91 (1994) 11427-11431.

Conyers, C. D., Lejeune, L., Shum, K., Gilbert, C., Shorr, R. G. L, Physiological effect of polyethylene glycol conjugation on stroma-free bovine hemoglobin in the conscious dog after partial exchange transfusion, Artificial organ, 21 (1997) 369-378.

Dyer, J. R., Use of periodate oxidation in biochemical analysis, Methods of Biochemical Analysis, 3 (1956) 111-152.

Fernandes, A. I., Gregoriadis, G., Polysialylated asparaginase: preparation, activity and pharmacokinetics, Biochimica et Biophysica Acta, 1341 (1997) 26-34.

Fernandes, A. I., Gregoriadis, G., The effect of polysialylation on the immunogenicity and antigenicity of asparaginase: implications in its pharmacokinetics, International Journal of Pharmaceutics, 217 (2001) 215-224.

Fernandes, A. I., Gregoriadis, G., Synthesis, characterization and properties of polysialylated catalase, Biochimica et Biophysica Acta, 1293 (1996) 92-96. [0172] Fleury, P., Lange, J., Sur l' oxydation des acides alcools et des sucres par l' acid periodique, Comptes Rendus Academic Sciences, 195 (1932) 1395-1397.

Gregoriadis, G., Drug and vaccine delivery systems, in: PharmaTech, World Markets Research Centre Limited, London (2001) 172-176.

Gregoriadis, G., Fernandes, A., McCormack, B., Mital, M., Zhang, X, Polysialic acids: Potential for long circulating drug, protein, liposome and other microparticle constructs, in Gregoriadis, G and McCormack, B (Eds), Targeting of Drugs, Stealth Therapeutic Systems, Plenum Press, New York (1998) 193-205.

Gregoriadis, G., Fernandes, A., Mital, M., McCormack, B., Polysialic acids: potential in improving the stability and pharmacokinetics of proteins and other therapeutics, Cellular and Molecular Life Sciences, 57 (2000) 1964-1969.

Gregoriadis, G., McCormack, B., Wang, Z., Lifely, R., Polysialic acids: potential in drug delivery, FEBS Letters, 315 (1993) 271-276.

Hreczuk-Hirst, D., Jain, S., Genkin, D., Laing, P., Gregoriadis, G., Preparation and properties of polysialylated interferon-.alpha.-2b, AAPS Annual Meeting, 2002, Toronto, Canada, M1056

Hunter, A. C, Moghimi, S. M., Therapeutic synthetic polymers: a game of Russian Roulette. Drug Discovery Today, 7 (2002) 998-1001.

Jain, S., Hirst, D. H., McCormack, B., Mital, M., Epenetos, A., Laing, P., Gregoriadis, G., Polysialylated insulin: synthesis, characterization and biological activity in vivo, Biochemica et. Biophysica Acta, 1622 (2003) 42-49.

Jain, S., Hirst, D. H., Laing, P., Gregoriadis, G., Polysialylation: The natural way to improve the stability and pharmacokinetics of protein and peptide drugs, Drug Delivery Systems and Sciences, 4(2) (2004) 3-9.

Jennings, H. J., Lugowski, C., Immunogenicity of groups A, B, and C meningococal polysaccharide tetanus toxoid conjugates, Journal of Immunology, 127 (1981) 1011-1018.

Lifely, R., Gilhert, A. S., Moreno, C. C., Sialic acid polysaccharide antigen of *Neisseria meningitidis* and *Escherichia coli*: esterification between adjacent residues, Carbohydrate Research, 94 (1981) 193-203.

Mital, M., Polysialic acids: a role for optimization of peptide and protein therapeutics, Ph.D. Thesis, University of London, 2004.

Muflenhoff, M., Ectehardt, M., Gerardy-Schohn, R., Polysialic acid: three-dimensional structure, biosynthesis and function, Current opinions in Structural Biology, 8 (1998) 558-564.

Park, J. T., Johnson, M. J., A submicrodetermination of glucose, Journal of Biological Chemistry, 181 (1949) 149-151.

Roth, J., Rutishauser, U., Troy, F. A. (Eds.), Polysialic acid: from microbes to man, Birkhauser Verlag, Basel, Advances in Life Sciences, 1993.

Rutishauser, U., Polysialic acid as regulator of cell interactions in: R. U. Morgoles and R. K. Margalis (eds.), Neurobiology of Glycoconjugates, pp 367-382, Plenum Press, New York, 1989.

Shriner, R. L., Fuson, R. D. C., Curtin, D. Y., Morill, T. C., The Systematic Identification of Organic Compounds, 6th ed., Wiley, New York, 1980.

Svennerholm, L., Quantitative estimation of sialic acid II: A colorimetric resorcinol-hydrochloric acid method, Biochimca et Biophysica Acta, 24 (1957) 604-611.

Troy, F. A. Polysialylation of neural cell adhesion molecules, Trends in Glycoscience and Glycotechnology, 2 (1990) 430-449.

Troy, F. A., Polysialylation: From bacteria to brain, Glycobiology, 2 (1992) 1-23.

The invention claimed is:

1. A process for producing an aldehyde derivative of a reducing terminal sialic acid of a starting material, which process comprises:
    a) providing a starting material having a terminal saccharide unit at a non-reducing end which has a vicinal diol group, wherein the starting material is subjected to a selective oxidation to oxidise the vicinal diol group at the non-reducing end to an aldehyde;
    b) reduction to reductively open a ring at the reducing terminal sialic acid unit, whereby a vicinal diol group is formed and the aldehyde at the non-reducing end is also reduced to form a hydroxy group which is not part of a vicinal diol group;
    c) selective oxidation to oxidise the vicinal diol group to form an aldehyde group at the reducing terminal sialic acid; and
    d) conjugating the aldehyde group at the reducing terminal sialic acid to a substrate.

2. A process according to claim 1 in which the saccharide unit at the non-reducing end is a sialic acid unit.

3. A process according to claim 1 in which the starting material is a di-, oligo- or poly-saccharide.

4. A process according to claim 3 in which the polysaccharide is a polysialic acid consisting essentially of units of sialic acid.

5. A process according to claim 3 in which a preliminary oxidation step is carried out under conditions such that there is substantially no mid-chain cleavage of the polysaccharide chain.

6. A process according to claim 1 wherein the substrate includes a peptide, a polypeptide, a protein, a protein therapeutic, a drug, a drug delivery system, a liposome, a virus, a cell, or a synthetic polymer.

7. A process according to claim 6 wherein the substrate is a polypeptide or a protein.

8. A process according to claim 6 wherein the substrate is a peptide or protein therapeutic.

9. A compound of formula II

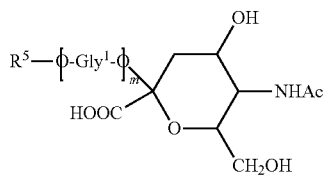

wherein Ac is acetyl;
m is 0 or more;
$Gly^1O$ is glycosyl; and
$R^5$ is an organic group conjugated to a reducing terminal sialic acid, wherein $R^5$ is selected from

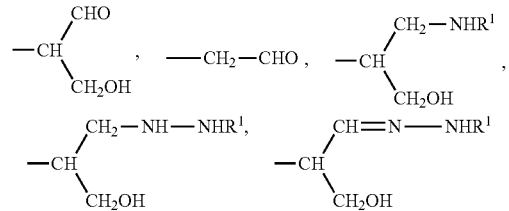

—$CH_2CH_2NHR^1$, $CH_2CH=N-NHR^1$ and $CH_2CH_2NHNHR^1$ and in which $R^1$ is H, $C_{1-24}$ alkyl, or aryl $C_{2-6}$ alkanoyl.

10. A compound according to claim 9 in which the groups GlyO comprise sialic acid units.

11. A compound according to claim 9 in which $R^1$ is a peptide, a polypeptide, a protein, a protein therapeutic, a drug, a drug delivery system, a liposome, a virus, a cell or a synthetic polymer.

12. A compound according to claim 11 in which $R^1$ is a polypeptide or protein.

13. A pharmaceutical composition comprising a compound according to claim 12 and a pharmaceutical excipient.

14. A compound according to claim 11 in which $R^1$ is a peptide or a protein therapeutic.

15. A pharmaceutical composition comprising a compound according to claim 14 and a pharmaceutical excipient.

16. A compound according to claim 9 in which $R^5$ is

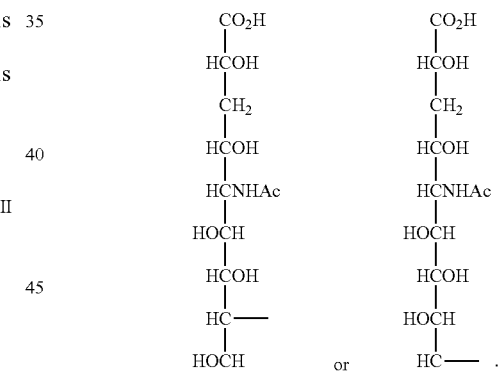

17. A composition comprising a compound according to claim 9 and a diluent.

* * * * *